US008801624B2

(12) United States Patent
Patangay et al.

(10) Patent No.: US 8,801,624 B2
(45) Date of Patent: *Aug. 12, 2014

(54) MONITORING OF HEART SOUNDS

(71) Applicant: Cardiac Pacemakers, Inc., St. Paul, MN (US)

(72) Inventors: Abhilash Patangay, Inver Grove Heights, MN (US); Jeffrey E. Stahmann, Ramsey, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/057,174

(22) Filed: Oct. 18, 2013

(65) Prior Publication Data

US 2014/0046200 A1     Feb. 13, 2014

Related U.S. Application Data

(63) Continuation of application No. 13/491,848, filed on Jun. 8, 2012, now Pat. No. 8,597,197, which is a continuation of application No. 11/777,739, filed on Jul. 13, 2007, now Pat. No. 8,211,034, which is a continuation-in-part of application No. 11/561,428, filed on Nov. 20, 2006, now abandoned.

(51) Int. Cl.
*A61B 7/04*         (2006.01)
(52) U.S. Cl.
USPC ........................................................ 600/528
(58) Field of Classification Search
None
See application file for complete search history.

(56) References Cited

U.S. PATENT DOCUMENTS

| 4,094,308 A | 6/1978 | Cormier |
| 4,220,160 A | 9/1980 | Kimball et al. |
| 4,289,141 A | 9/1981 | Cormier |

(Continued)

FOREIGN PATENT DOCUMENTS

| AU | 2008241508 | 2/2012 |
| EP | 0762908 B1 | 3/1997 |

(Continued)

OTHER PUBLICATIONS

"U.S. Appl. No. 10/334,694, Advisory Action mailed Dec. 18, 2007", 3 pgs.

(Continued)

*Primary Examiner* — Paula J Stice
(74) *Attorney, Agent, or Firm* — Schwegman, Lundberg & Woessner, P.A.

(57) ABSTRACT

This document discusses, among other things, a system comprising an implantable medical device (IMD) including an implantable heart sound sensor circuit configured to produce an electrical heart sound signal representative of a heart sound of a subject and a processor circuit. The processor circuit is coupled to the heart sound sensor circuit and includes a detection circuit, a heart sound feature circuit and a trending circuit. The detection circuit configured to detect a physiologic perturbation and the heart sound feature circuit is configured to identify a heart sound feature in the electrical signal. The processor circuit is configured to trigger the heart sound feature circuit in relation to a detected physiologic perturbation. The trending circuit is configured to trend the heart sound feature in relation to a recurrence of the physiologic perturbation. The processor circuit is configured to declare a change in a physiologic condition of the patient according to the trending.

20 Claims, 8 Drawing Sheets

(56) References Cited

U.S. PATENT DOCUMENTS

| | | |
|---|---|---|
| 4,428,380 A | 1/1984 | Wong et al. |
| 4,446,872 A | 5/1984 | Marsoner et al. |
| 4,548,204 A | 10/1985 | Groch et al. |
| 4,586,514 A | 5/1986 | Schlager et al. |
| 4,628,939 A | 12/1986 | Little et al. |
| 4,649,930 A | 3/1987 | Groch et al. |
| 4,702,253 A | 10/1987 | Nappholz et al. |
| 4,763,646 A | 8/1988 | Lekholm |
| 4,773,401 A | 9/1988 | Citak et al. |
| 4,796,639 A | 1/1989 | Snow et al. |
| 4,905,706 A | 3/1990 | Duff et al. |
| 4,915,113 A | 4/1990 | Holman |
| 4,967,760 A | 11/1990 | Bennett et al. |
| 4,981,139 A | 1/1991 | Pfohl |
| 4,989,611 A | 2/1991 | Zanetti et al. |
| 5,010,889 A | 4/1991 | Bredesen et al. |
| 5,012,815 A | 5/1991 | Bennett et al. |
| 5,025,809 A | 6/1991 | Johnson et al. |
| 5,159,932 A | 11/1992 | Zanetti et al. |
| 5,179,947 A | 1/1993 | Meyerson et al. |
| 5,190,035 A | 3/1993 | Salo et al. |
| 5,218,969 A | 6/1993 | Bredesen et al. |
| 5,301,679 A | 4/1994 | Taylor |
| 5,305,745 A | 4/1994 | Zacouto |
| 5,337,752 A | 8/1994 | Reeves |
| 5,365,932 A | 11/1994 | Greenhut |
| 5,496,361 A | 3/1996 | Moberg et al. |
| 5,540,727 A | 7/1996 | Tockman et al. |
| 5,544,661 A | 8/1996 | Davis et al. |
| 5,554,177 A | 9/1996 | Kieval et al. |
| 5,630,835 A | 5/1997 | Brownlee |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,792,195 A | 8/1998 | Carlson et al. |
| 5,836,987 A | 11/1998 | Baumann et al. |
| 5,860,933 A | 1/1999 | Don Michael |
| 5,911,738 A | 6/1999 | Sikorski et al. |
| 5,935,081 A | 8/1999 | Kadhiresan |
| 5,957,866 A | 9/1999 | Shapiro et al. |
| 5,974,340 A | 10/1999 | Kadhiresan |
| 5,991,661 A | 11/1999 | Park et al. |
| 6,002,777 A | 12/1999 | Grasfield et al. |
| 6,022,963 A | 2/2000 | McGall et al. |
| 6,044,298 A | 3/2000 | Salo et al. |
| 6,044,299 A | 3/2000 | Nilsson |
| 6,045,513 A | 4/2000 | Stone et al. |
| 6,053,872 A | 4/2000 | Mohler |
| 6,058,329 A | 5/2000 | Salo et al. |
| 6,064,910 A | 5/2000 | Andersson et al. |
| 6,076,015 A | 6/2000 | Hartley et al. |
| 6,077,227 A | 6/2000 | Miesel et al. |
| 6,144,880 A | 11/2000 | Ding et al. |
| 6,152,884 A | 11/2000 | Bjorgaas |
| 6,161,042 A | 12/2000 | Hartley et al. |
| 6,193,668 B1 | 2/2001 | Chassaing et al. |
| 6,208,900 B1 | 3/2001 | Ecker et al. |
| 6,243,606 B1 | 6/2001 | Mann et al. |
| 6,264,611 B1 | 7/2001 | Ishikawa et al. |
| 6,269,396 B1 | 7/2001 | Shah et al. |
| 6,272,377 B1 | 8/2001 | Sweeney et al. |
| 6,298,269 B1 | 10/2001 | Sweeney |
| 6,312,378 B1 | 11/2001 | Bardy |
| 6,327,622 B1 | 12/2001 | Jindal et al. |
| 6,351,673 B1 | 2/2002 | Ding et al. |
| 6,360,127 B1 | 3/2002 | Ding et al. |
| 6,366,811 B1 | 4/2002 | Carlson |
| 6,368,283 B1 | 4/2002 | Xu et al. |
| 6,409,675 B1 | 6/2002 | Turcott |
| 6,411,840 B1 | 6/2002 | Bardy |
| 6,415,033 B1 | 7/2002 | Halleck et al. |
| 6,440,082 B1 | 8/2002 | Joo et al. |
| 6,459,929 B1 | 10/2002 | Hopper et al. |
| 6,463,326 B1 | 10/2002 | Hartley et al. |
| 6,477,406 B1 | 11/2002 | Turcott |
| 6,478,746 B2 | 11/2002 | Chassaing et al. |
| 6,480,733 B1 | 11/2002 | Turcott |
| 6,491,639 B1 | 12/2002 | Turcott |
| 6,520,924 B2 | 2/2003 | Lee |
| 6,527,729 B1 | 3/2003 | Turcott |
| 6,542,775 B2 | 4/2003 | Ding et al. |
| 6,575,916 B2 | 6/2003 | Halleck et al. |
| 6,626,842 B2 | 9/2003 | Oka |
| 6,629,937 B2 | 10/2003 | Watrous |
| 6,643,548 B1 | 11/2003 | Mai et al. |
| 6,643,584 B1 | 11/2003 | Ikeuchi et al. |
| 6,650,940 B1 | 11/2003 | Zhu et al. |
| 6,665,564 B2 | 12/2003 | Lincoln et al. |
| 6,666,826 B2 | 12/2003 | Salo et al. |
| 6,684,103 B2 | 1/2004 | Ding et al. |
| 6,733,464 B2 | 5/2004 | Olbrich et al. |
| 6,741,886 B2 | 5/2004 | Yonce |
| 6,792,308 B2 | 9/2004 | Corbucci |
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,830,548 B2 | 12/2004 | Bonnet et al. |
| 6,845,263 B2 | 1/2005 | Kawaguchi |
| 6,868,346 B2 | 3/2005 | Larson et al. |
| 6,942,622 B1 | 9/2005 | Turcott |
| 6,949,075 B2 | 9/2005 | Hatlestad et al. |
| 6,980,851 B2 | 12/2005 | Zhu et al. |
| 6,999,816 B2 | 2/2006 | Van |
| 7,039,462 B2 | 5/2006 | Pastore et al. |
| 7,052,466 B2 | 5/2006 | Scheiner et al. |
| 7,096,060 B2 | 8/2006 | Arand et al. |
| 7,110,817 B2 | 9/2006 | Yu et al. |
| 7,115,096 B2 | 10/2006 | Siejko et al. |
| 7,123,962 B2 | 10/2006 | Siejko et al. |
| 7,127,290 B2 | 10/2006 | Girouard et al. |
| 7,139,609 B1 | 11/2006 | Min et al. |
| 7,158,830 B2 | 1/2007 | Yu et al. |
| 7,174,203 B2 | 2/2007 | Arand et al. |
| 7,209,786 B2 | 4/2007 | Brockway et al. |
| 7,215,997 B2 | 5/2007 | Yu et al. |
| 7,226,422 B2 | 6/2007 | Hatlestsad et al. |
| 7,248,923 B2 | 7/2007 | Maile et al. |
| 7,269,458 B2 | 9/2007 | Kadhiresan et al. |
| 7,387,610 B2 | 6/2008 | Stahmann et al. |
| 7,400,928 B2 | 7/2008 | Hatlestad |
| 7,424,321 B2 | 9/2008 | Wariar et al. |
| 7,431,699 B2 | 10/2008 | Siejko et al. |
| 7,479,112 B2 | 1/2009 | Sweeney et al. |
| 7,480,528 B2 | 1/2009 | Brockway et al. |
| 7,559,901 B2 | 7/2009 | Maile et al. |
| 7,582,061 B2 | 9/2009 | Li et al. |
| 7,585,279 B2 | 9/2009 | Carlson et al. |
| 7,662,104 B2 | 2/2010 | Siejko et al. |
| 7,678,061 B2 | 3/2010 | Lee et al. |
| 7,713,213 B2 | 5/2010 | Siejko et al. |
| 7,736,319 B2 | 6/2010 | Patangay et al. |
| 7,780,606 B2 | 8/2010 | Carlson et al. |
| 7,853,327 B2 | 12/2010 | Patangay et al. |
| 7,917,210 B2 | 3/2011 | Baynham et al. |
| 7,922,669 B2 | 4/2011 | Zhang et al. |
| 7,938,781 B2 | 5/2011 | Carlson et al. |
| 8,096,954 B2 | 1/2012 | Stahmann et al. |
| 8,211,033 B2 | 7/2012 | Siejko et al. |
| 8,211,034 B2 * | 7/2012 | Patangay et al. ............... 600/528 |
| 8,257,271 B2 | 9/2012 | Siejko et al. |
| 8,332,034 B2 | 12/2012 | Patangay et al. |
| 8,597,197 B2 * | 12/2013 | Patangay et al. ............... 600/528 |
| 2002/0001390 A1 | 1/2002 | Kawaguchi |
| 2002/0035337 A1 | 3/2002 | Oka |
| 2002/0072684 A1 | 6/2002 | Stearns |
| 2002/0082645 A1 | 6/2002 | Sweeney |
| 2002/0107450 A1 | 8/2002 | Ogura |
| 2002/0128563 A1 | 9/2002 | Carlson et al. |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0055352 A1 | 3/2003 | Hayek et al. |

(56) References Cited

U.S. PATENT DOCUMENTS

| | | |
|---|---|---|
| 2003/0055461 A1 | 3/2003 | Girouard et al. |
| 2003/0069608 A1 | 4/2003 | Sweeney |
| 2003/0072458 A1 | 4/2003 | Halleck et al. |
| 2003/0093002 A1 | 5/2003 | Kuo |
| 2003/0093003 A1 | 5/2003 | Watrous et al. |
| 2003/0105497 A1 | 6/2003 | Zhu et al. |
| 2003/0120159 A1 | 6/2003 | Mohler |
| 2003/0144702 A1 | 7/2003 | Yu et al. |
| 2003/0144703 A1 | 7/2003 | Yu et al. |
| 2003/0158492 A1 | 8/2003 | Sheldon et al. |
| 2003/0158584 A1 | 8/2003 | Cates et al. |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2003/0233132 A1 | 12/2003 | Pastore et al. |
| 2004/0024423 A1 | 2/2004 | Lincoln et al. |
| 2004/0039295 A1 | 2/2004 | Olbrich et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0078059 A1 | 4/2004 | Ding et al. |
| 2004/0078060 A1 | 4/2004 | Ding et al. |
| 2004/0102712 A1 | 5/2004 | Belalcazar et al. |
| 2004/0106960 A1 | 6/2004 | Siejko et al. |
| 2004/0106961 A1 | 6/2004 | Siejko et al. |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0004485 A1 | 1/2005 | Crosby et al. |
| 2005/0027323 A1 | 2/2005 | Mulligan et al. |
| 2005/0033190 A1 | 2/2005 | Bauer |
| 2005/0065448 A1 | 3/2005 | Stahmann et al. |
| 2005/0065556 A1 | 3/2005 | Reghabi et al. |
| 2005/0102001 A1 | 5/2005 | Maile et al. |
| 2005/0107838 A1 | 5/2005 | Lovett et al. |
| 2005/0115561 A1 | 6/2005 | Stahmann et al. |
| 2005/0137626 A1 | 6/2005 | Pastore et al. |
| 2005/0148896 A1 | 7/2005 | Siejko et al. |
| 2005/0149136 A1 | 7/2005 | Siejko et al. |
| 2005/0222515 A1 | 10/2005 | Polyshchuk et al. |
| 2006/0020294 A1 | 1/2006 | Brockway et al. |
| 2006/0020295 A1 | 1/2006 | Brockway et al. |
| 2006/0030892 A1 | 2/2006 | Kadhiresan et al. |
| 2006/0047213 A1 | 3/2006 | Gavriely et al. |
| 2006/0161070 A1 | 7/2006 | Siejko et al. |
| 2006/0247550 A1 | 11/2006 | Thiagarajan et al. |
| 2006/0270939 A1 | 11/2006 | Wariar et al. |
| 2006/0282000 A1 | 12/2006 | Zhang et al. |
| 2007/0054871 A1 | 3/2007 | Pastore et al. |
| 2007/0078491 A1 | 4/2007 | Siejko et al. |
| 2007/0123943 A1 | 5/2007 | Patangay et al. |
| 2007/0191725 A1 | 8/2007 | Nelson |
| 2007/0239218 A1 | 10/2007 | Carlson et al. |
| 2008/0015651 A1 | 1/2008 | Ettori et al. |
| 2008/0103406 A1 | 5/2008 | Kameli |
| 2008/0119749 A1 | 5/2008 | Haro et al. |
| 2008/0119750 A1 | 5/2008 | Patangay et al. |
| 2008/0125820 A1 | 5/2008 | Stahmann et al. |
| 2008/0177191 A1 | 7/2008 | Patangay et al. |
| 2008/0262368 A1 | 10/2008 | Patangay et al. |
| 2009/0018461 A1 | 1/2009 | Siejko et al. |
| 2009/0132000 A1 | 5/2009 | Brockway et al. |
| 2009/0287106 A1 | 11/2009 | Zhang et al. |
| 2010/0249863 A1 | 9/2010 | Carlson et al. |
| 2011/0077543 A1 | 3/2011 | Patangay et al. |
| 2011/0098588 A1 | 4/2011 | Siejko et al. |
| 2012/0089040 A1 | 4/2012 | Stahmann et al. |
| 2012/0271186 A1 | 10/2012 | Siejko et al. |
| 2012/0310099 A1 | 12/2012 | Patangay et al. |
| 2013/0096451 A1 | 4/2013 | Patangay et al. |

FOREIGN PATENT DOCUMENTS

| | | |
|---|---|---|
| EP | 1179317 A2 | 2/2002 |
| EP | 1247485 A1 | 10/2002 |
| JP | 2006512168 A | 4/2006 |
| WO | WO-0156651 A1 | 8/2001 |
| WO | WO-2004012815 A1 | 2/2004 |
| WO | WO-2004035137 A1 | 4/2004 |
| WO | WO-2004050178 A1 | 6/2004 |
| WO | WO-2004060483 A1 | 7/2004 |
| WO | WO-2006028575 A2 | 3/2006 |
| WO | WO-2006028575 A3 | 3/2006 |
| WO | WO-2006127594 A2 | 11/2006 |
| WO | WO-2006127594 A3 | 11/2006 |
| WO | WO-2008063288 A2 | 5/2008 |
| WO | WO-2008063288 A3 | 5/2008 |
| WO | WO-2008130532 A1 | 10/2008 |

OTHER PUBLICATIONS

"U.S. Appl. No. 10/334,694, Advisory Action mailed Dec. 23, 2008", 3 pgs.

"U.S. Appl. No. 10/334,694, Final Office Action mailed Oct. 1, 2007", 13 pgs.

"U.S. Appl. No. 10/334,694, Final Office Action mailed Oct. 7, 2008", 14 pgs.

"U.S. Appl. No. 10/334,694, Final Office Action mailed Nov. 27, 2009", 13 pgs.

"U.S. Appl. No. 10/334,694, Non-Final Office Action mailed Mar. 18, 2009", 14 pgs.

"U.S. Appl. No. 10/334,694, Non-Final Office Action mailed Mar. 19, 2008", 15 pgs.

"U.S. Appl. No. 10/334,694, Non-Final Office Action mailed Apr. 20, 2007", 12 pgs.

"U.S. Appl. No. 10/334,694, Non-Final Office Action mailed Apr. 30, 2010", 13 pgs.

"U.S. Appl. No. 10/334,694, Non-Final Office Action mailed Nov. 27, 2006", 9 pgs.

"U.S. Appl. No. 10/334,694, Notice of Allowance mailed Oct. 5, 2010", 6 pgs.

"U.S. Appl. No. 10/334,694, Response filed Feb. 27, 2007 to Non-Final Office Action mailed Nov. 27, 2006", 20 pgs.

"U.S. Appl. No. 10/334,694, Response filed Mar. 1, 2010 to Final Office Action mailed Nov. 27, 2009", 21 pgs.

"U.S. Appl. No. 10/334,694, Response filed Jun. 19, 2008 to Non-Final Office Action mailed Mar. 19, 2008", 20 pgs.

"U.S. Appl. No. 10/334,694, Response filed Jul. 17, 2009 to Non Final Office Action mailed Mar. 18, 2009", 18 pgs.

"U.S. Appl. No. 10/334,694, Response filed Jul. 20, 2007 to Non-Final Office Action mailed Apr. 20, 2007", 18 pgs.

"U.S. Appl. No. 10/334,694, Response filed Jul. 27, 2010 to Non Final Office Action mailed Apr. 30, 2010", 19 pgs.

"U.S. Appl. No. 10/334,694, Response filed Dec. 3, 2007 to Final Office Action mailed Oct. 1, 2007", 21 pgs.

"U.S. Appl. No. 10/334,694, Response filed Dec. 8, 2008 to Final Office Action mailed Oct. 7, 2008", 18 pgs.

"U.S. Appl. No. 10/746,853, Final Office Action mailed May 22, 2007", 11 pgs.

"U.S. Appl. No. 10/746,853, Non-Final Office Action mailed Sep. 26, 2007", 8 pgs.

"U.S. Appl. No. 10/746,853, Non-Final Office Action mailed Dec. 19, 2006", 10 pgs.

"U.S. Appl. No. 10/746,853, Notice of Allowance mailed May 30, 2008", 4 pgs.

"U.S. Appl. No. 10/746,853, Response filed Jan. 17, 2008 to Non-Final Office Action mailed Sep. 26, 2007", 18 pgs.

"U.S. Appl. No. 10/746,853, Response filed Mar. 15, 2007 to Non-Final Office Action mailed Dec. 19, 2006", 16 pgs.

"U.S. Appl. No. 10/746,853, Response filed Jul. 23, 2007 to Final Office Action mailed May 22, 2007", 16 pgs.

(56) References Cited

OTHER PUBLICATIONS

"U.S. Appl. No. 10/746,874, Notice of Allowance mailed May 19, 2006", 9 pgs.
"U.S. Appl. No. 10/746,874, Response filed Apr. 17, 2006 to Restriction Requirement mailed Mar. 31, 2006", 14 pgs.
"U.S. Appl. No. 10/746,874, Restriction Requirement mailed Mar. 31, 2006", 6 pgs.
"U.S. Appl. No. 10/865,498, Non-Final Office Action mailed Sep. 11, 2006", 11 pgs.
"U.S. Appl. No. 10/865,498, Notice of Allowance mailed Dec. 6, 2006", 12 pgs.
"U.S. Appl. No. 10/865,498, Response filed Oct. 24, 2006 to Non-Final Office Action mailed Sep. 11, 2006", 19 pgs.
"U.S. Appl. No. 11/148,107, Notice of Allowance mailed Aug. 30, 2010", 8 pgs.
"U.S. Appl. No. 11/277,773, Examiner Interview Summary mailed Oct. 2, 2008", 2 pgs.
"U.S. Appl. No. 11/277,773, Notice of Allowance mailed Mar. 24, 2010", 6 pgs.
"U.S. Appl. No. 11/426,835, Final Office Action mailed Nov. 12, 2010", 13 pgs.
"U.S. Appl. No. 11/426,835, Non-Final Office Action mailed Apr. 1, 2010", 13 pgs.
"U.S. Appl. No. 11/426,835, Response filed Aug. 2, 2010 to Non Final Office Action mailed Apr. 1, 2010", 16 pgs.
"U.S. Appl. No. 11/426,835, Response filed Nov. 6, 20009 to Restriction Requirement mailed Oct. 6, 2009", 12 pgs.
"U.S. Appl. No. 11/465,878, Notice of Allowance mailed Mar. 5, 2012", 7 pgs.
"U.S. Appl. No. 11/465,878, Notice of Allowance mailed Oct. 8, 2009", 8 pgs.
"U.S. Appl. No. 11/561,428, Final Office Action mailed Feb. 10, 2011", 19 pgs.
"U.S. Appl. No. 11/561,428, Non Final Office Action mailed Apr. 20, 2010", 13 pgs.
"U.S. Appl. No. 11/561,428, Response filed Oct. 20, 2010 to Non Final Office Action mailed Apr. 20, 2010", 15 pgs.
"U.S. Appl. No. 11/564,637, Examiner Interview Summary mailed Feb. 18, 2010", 5 pgs.
"U.S. Appl. No. 11/564,637, Examiner Interview Summary mailed Aug. 11, 2009", 4 pgs.
"U.S. Appl. No. 11/564,637, Final Office Action mailed Dec. 10, 2009", 9 pgs.
"U.S. Appl. No. 11/564,637, Non Final Office Action mailed Mar. 29, 2011", 9 pgs.
"U.S. Appl. No. 11/564,637, Non-Final Office Action mailed May 13, 2009", 7 pgs.
"U.S. Appl. No. 11/564,637, Notice of Allowance mailed Sep. 22, 2011", 10 pgs.
"U.S. Appl. No. 11/564,637, Response filed Feb. 23, 2010 to Final Office Action mailed Dec. 10, 2009", 9 pgs.
"U.S. Appl. No. 11/564,637, Response filed Apr. 16, 2009 to Restriction Requirement mailed Mar. 16, 2009", 6 pgs.
"U.S. Appl. No. 11/564,637, Response filed Jun. 28, 2011 to Non-Final Office Action mailed Mar. 29, 2011", 11 pgs.
"U.S. Appl. No. 11/564,637, Response filed Aug. 13, 2009 to Non Final Office Action mailed May 13, 2009", 7 pgs.
"U.S. Appl. No. 11/564,637, Restriction Requirement mailed Mar. 16, 2009", 6 pgs.
"U.S. Appl. No. 11/736,055, Non-Final Office Action mailed Mar. 12, 2010", 7 pgs.
"U.S. Appl. No. 11/736,055, Notice of Allowance mailed Aug. 13, 2010", 8 pgs.
"U.S. Appl. No. 11/736,055, Response filed Jul. 2, 2010 to Non Final Office Action mailed Mar. 12, 2010", 17 pgs.
"U.S. Appl. No. 11/777,739, Corrected Notice of Allowability mailed Apr. 9, 2012", 5 pgs.
"U.S. Appl. No. 11/777,739, Examiner Interview Summary mailed Apr. 29, 2010", 3 pgs.
"U.S. Appl. No. 11/777,739, Final Office Action mailed Jun. 4, 2010", 16 pgs.
"U.S. Appl. No. 11/777,739, Issue Notification mailed Jun. 15, 2012", 1 pg.
"U.S. Appl. No. 11/777,739, Non Final Office Action mailed Jan. 29, 2010", 18 pgs.
"U.S. Appl. No. 11/777,739, Non Final Office Action mailed Nov. 18, 2011", 6 pgs.
"U.S. Appl. No. 11/777,739, Notice of Allowance mailed Feb. 29, 2012", 9 pgs.
"U.S. Appl. No. 11/777,739, Response filed Feb. 14, 2012 to Non Final Office Action mailed Nov. 18, 2011", 15 pgs.
"U.S. Appl. No. 11/777,739, Response filed Apr. 29, 2010 to Non Final Office Action mailed Jan. 29, 2010", 18 pgs.
"U.S. Appl. No. 11/777,739, Response filed Aug. 4, 2010 to Final Office Action mailed Jun. 4, 2010", 16 pgs.
"U.S. Appl. No. 11/777,739, Response filed Oct. 19, 2009 to Restriction Requirement mailed Sep. 23, 2009", 9 pgs.
"U.S. Appl. No. 11/777,739, Response to 312 Amendment mailed Jun. 5, 2012", 2 pgs.
"U.S. Appl. No. 11/777,739, Restriction Requirement mailed Sep. 23, 2009", 7 pgs.
"U.S. Appl. No. 12/283,760, Final Office Action mailed Apr. 24, 2012", 16 pgs.
"U.S. Appl. No. 12/283,760, Non Final Office Action mailed Oct. 5, 2011", 9 pgs.
"U.S. Appl. No. 12/283,760, Response filed Feb. 6, 2012 to Non Final Office Action mailed Oct. 5, 2011", 15 pgs.
"U.S. Appl. No. 12/813,073, Non-Final Office Action mailed Sep. 3, 2010", 7 pgs.
"U.S. Appl. No. 12/963,902, Final Office Action mailed May 29, 2012", 7 pgs.
"U.S. Appl. No. 12/964,902, Examiner Interview Summary mailed Apr. 23, 2012", 3 pgs.
"U.S. Appl. No. 12/964,902, Non Final Office Action Mailed Dec. 21, 2011", 8 pgs.
"U.S. Appl. No. 12/964,902, Notice of Allowance mailed Aug. 1, 2012", 8 pgs.
"U.S. Appl. No. 12/964,902, Response filed Apr. 23, 2012 to Non-Final Office Action mailed Dec. 21, 2011", 16 pgs.
"U.S. Appl. No. 12/964,902, Response filed Jul. 12, 2012 to Final Office Action mailed May 29, 2012", 13 pgs.
"U.S. Appl. No. 13/491,848 , Response filed Jul. 25, 2013 to Final Office Action mailed Jul. 12, 2013", 9 pgs.
"U.S. Appl. No. 13/491,848, Final Office Action mailed Jul. 12, 2013", 7 pgs.
"U.S. Appl. No. 13/491,848, Non Final Office Action mailed Mar. 29, 2013", 13 pgs.
"U.S. Appl. No. 13/491,848, Notice of Allowance mailed Aug. 6, 2013", 9 pgs.
"U.S. Appl. No. 13/491,848, Response filed May 22, 2013 to Non Final Office Action mailed Mar. 29, 2013", 12 pgs.
"U.S. Appl. No. 13/708,196, Non Final Office Action mailed May 8, 2013", 9 pgs.
"Australian Application Serial No. 2008241508, First Examiner Report mailed Nov. 23, 2010", 3 Pgs.
"Australian Application Serial No. 2008241508, Response filed Sep. 16, 2011 to Office Action mailed Nov. 23, 2010", 29 pgs.
"European Application Serial No. 05806944.4, Office Action mailed Apr. 14, 2008", 8 pgs.
"European Application Serial No. 05806944.4, Response filed Oct. 17, 2008 to Office Action mailed Apr. 14, 2008", 22 pgs.
"European Application Serial No. 07753005.3, Communication dated Nov. 5, 2008", 2 pgs.
"European Application Serial No. 07753005.3, Response filed Dec. 2, 2008 to Communication dated Nov. 5, 2008", 9 pgs.
"European Application Serial No. 08742888.4, Office Action mailed Feb. 12, 2010", 2 pgs.
"European Application Serial No. 08742888.4, Response filed Aug. 10, 2010 to Office Action mailed Feb. 12, 2010", 25 pgs.
"International Application Serial No. PCT/US2005/025235, International Search Report and Written Opinion mailed Apr. 4, 2006", 20 pgs.

(56) References Cited

OTHER PUBLICATIONS

"International Application Serial No. PCT/US2005/025235, Invitation to Pay Additional Fees and Partial Search Report mailed Jan. 27, 2006", 9 pgs.
"International Application Serial No. PCT/US2007/021503, International Search Report mailed Jun. 5, 2008", 4 pgs.
"International Application Serial No. PCT/US2007/021503, Written Opinion mailed Jun. 5, 2008", 7 pgs.
"International Application Serial No. PCT/US2008/004832, International Search Report mailed Sep. 3, 2008", 6 pgs.
"International Application Serial No. PCT/US2008/004832, International Written Opinion mailed Sep. 3, 2008", 7 pgs.
"International Application Serial No. PCT/US2008/004832, Written Opinion mailed Sep. 3, 2008", 7 pgs.
"Japanese Application Serial No. 2009-502827, Amended Claims filed Mar. 4, 2010", (w/ English Translation), 15 pgs.
"Japanese Application Serial No. 2010-504062, Office Action mailed Jan. 17, 2012", (w/ English Translation), 6 pgs.
"Japanese Application Serial No. 2010-504062, Response filed May 17, 2012 to Office Action mailed Jan. 17, 2012", (w/ English Translation), 9 pgs.
Aaron, S. D, et al., "How accurate is spirometry at predicting restrictive pulmonary impairment?", Chest, 115(3), XP002362629 ISSN: 0012-3692, (Mar. 1999), 869-873.
Bulgrin, J. R, et al., "Comparison of Short-Time Fourier, Wavelet and Time-Domain Analyses of Intracardiac Sounds", Biomedical Sciences Instrumentation, 29, (1993), 4 pgs.
Carlson, Gerrard M, et al., "Managing Preload Reserve by Tracking the Ventricular Operating Point With Heart Sounds", U.S. Appl. No. 11/189,462 filed Jul. 26, 2005, 36 pgs.
Dreuw, P., et al., "Tracking Using Dynamic Programming for Appearance-Based Sign Language Recognition", Proceedings of the 7th International Conference on Automatic Face and Gesture Recognition, (2006), 293-298.
Kinderman, Michael, et al., "Optimizing the AV Delay in DDD Pacemaker Patients with High Degree AV Block: Mitral Valve Doppler Versus Impedance Cardiography", PACE, vol. 20, (Oct. 1997), 2453-2462.
Leatham, A, "Splitting of the First and Second Heart Sounds", Lancet, 267 (6839), (Sep. 25, 1954), 607-614.
Leonelli, Fabio M, et al., "Systolic and Diastolic Effects of Variable Atroventricular Delay and Patients with Complete Hear Block and Normal Ventricular Function", Amer. J-Cardiology, vol. 80, (Aug. 1, 1997), 294-298.
Makhoul, John, "Linear Prediction: A Tutorial Review", Proceedings of the IEEE, 63, (Apr. 1975), 561-580.
Marcus, G. M., et al., "Association Between Phonocardiographic Third and Fourth Heart Sounds and Objective Measures of Left Ventricular Function", JAMA, 293(18), (May 11, 2005), 2238-44.
Obaidat, M. S, et al., "Performance of the Short-Time Fourier Transform and Wavelet Transform to Phonocardiogram Signal Analysis", Proceedings of the 1992 ACM/SIGAPP Symposium on Applied Computing ACM, Applied Computing: Technological Challenges of the 1990s, (1992), 856-862.
Ritter, P., et al., "New Method for Determining the Optimal Atrio-Ventricular Delay in Patients Place in DDD Mode for Complete Atrio-Ventricular Block", NASPE Abstracts, (Abstract No. 237), (1995), 3 pgs.
Tavel, Morton E, "The Appearance of Gallop Rhythm after Exercise Stress Testing", Clin. Cardiol., vol. 19, (1996), 887-891.
"U.S. Appl. No. 10/334,694, Notice of Allowance mailed Mar. 4, 2011", 7 pgs.
"U.S. Appl. No. 10/795,126, Notice of Allowance mailed Jul. 9, 2007", 10 pgs.
"U.S. Appl. No. 10/795,126, Response filed Apr. 25, 2007 to Non Final Office Action mailed Jan. 25, 2007", 11 pgs.
"U.S. Appl. No. 10/865,498, Response filed Oct. 24, 2006 to Non Final Office Action mailed Sep. 11, 2006", 19 pgs.
"U.S. Appl. No. 10/897,856, Advisory Action mailed Jun. 17, 2008", 3 pgs.
"U.S. Appl. No. 10/897,856, Final Office Action mailed Jan. 4, 2008", 15 pgs.
"U.S. Appl. No. 10/897,856, Non Final Office Action mailed Oct. 4, 2006", 15 pgs.
"U.S. Appl. No. 10/897,856, Notice of Allowance mailed Sep. 15, 2008", 6 pgs.
"U.S. Appl. No. 10/897,856, Response filed Jan. 2, 2007 to Non Final Office Action mailed Oct. 4, 2006", 24 pgs.
"U.S. Appl. No. 10/897,856, Response filed Mar. 4, 2008 to Final Office Action mailed Jan. 4, 2008", 24 pgs.
"U.S. Appl. No. 10/897,856, Supplemental Notice of Allowability mailed Oct. 22, 2008", 3 pgs.
"U.S. Appl. No. 10/897,856, Supplemental Notice of Allowability mailed Dec. 3, 2008", 3 pgs.
"U.S. Appl. No. 10/900,570, Non-Final Office Action mailed Jan. 10, 2008", 4 pgs.
"U.S. Appl. No. 10/900,570, Non-Final Office Action mailed Jul. 25, 2008", 5 pgs.
"U.S. Appl. No. 10/900,570, Notice of Allowance mailed Mar. 6, 2009", 6 pgs.
"U.S. Appl. No. 10/900,570, Response filed Apr. 10, 2008 to Non-Final Office Action mailed Jan. 10, 2008", 7 pgs.
"U.S. Appl. No. 10/900,570, Response filed Oct. 22, 2007 to Restriction Requirement mailed Sep. 27, 2007", 7 pgs.
"U.S. Appl. No. 10/900,570, Response filed Nov. 25, 2008 to Non Final Office Action mailed Jul. 25, 2008", 9 pgs.
"U.S. Appl. No. 10/900,570, Restriction Requirement mailed Sep. 27, 2007", 6 pgs.
"U.S. Appl. No. 11/037,275, Examiner Interview Summary mailed Apr. 20, 2009", 2 pgs.
"U.S. Appl. No. 11/037,275, Examiner Interview Summary mailed Sep. 5, 2008", 2 pgs.
"U.S. Appl. No. 11/037,275, Final Office Action mailed Jun. 17, 2008", 12 pgs.
"U.S. Appl. No. 11/037,275, Final Office Action mailed Jun. 17, 2009", 11 pgs.
"U.S. Appl. No. 11/037,275, Non-Final Office Action mailed Jan. 15, 2009", 9 pgs.
"U.S. Appl. No. 11/037,275, Non-Final Office Action mailed Dec. 12, 2007", 17 pgs.
"U.S. Appl. No. 11/037,275, Notice of Allowance mailed Sep. 23, 2009", 6 pgs.
"U.S. Appl. No. 11/037,275, Response filed Mar. 12, 2008 to Non Final Office Action mailed Dec. 12, 2007", 16 pgs.
"U.S. Appl. No. 11/037,275, Response filed Apr. 15, 2009 to Non Final Office Action mailed Jan. 15, 2009", 12 pgs.
"U.S. Appl. No. 11/037,275, Response filed Aug. 13, 2009 to Final Office Action mailed Jun. 17, 2009", 14 pgs.
"U.S. Appl. No. 11/037,275, Response filed Sep. 17, 2008 to Final Office Action mailed Jun. 17, 2008", 12 pgs.
"U.S. Appl. No. 11/113,828, Final Office Action mailed Sep. 17, 2008", 10 pgs.
"U.S. Appl. No. 11/113,828, Non Final Office Action mailed Mar. 5, 2008", 8 pgs.
"U.S. Appl. No. 11/113,828, Non Final Office Action mailed Dec. 22, 2008", 10 pgs.
"U.S. Appl. No. 11/113,828, Response filed Jan. 28, 2008 to Restriction Requirement mailed Dec. 26, 2007", 7 pgs.
"U.S. Appl. No. 11/113,828, Response filed Mar. 23, 2009 to Non Final Office Action mailed Dec. 22, 2008", 8 pgs.
"U.S. Appl. No. 11/113,828, Response filed Jun. 5, 2008 to Non Final Office Action mailed Mar. 5, 2008", 8 pgs.
"U.S. Appl. No. 11/113,828, Response filed Nov. 17, 2008 to Final Office Action mailed Sep. 17, 2008", 11 pgs.
"U.S. Appl. No. 11/113,828, Restriction Requirement mailed Dec. 26, 2007", 8 pgs.
"U.S. Appl. No. 11/129,050, Advisory Action mailed Jul. 14, 2009", 3 pgs.
"U.S. Appl. No. 11/129,050, Advisory Action mailed Jul. 28, 2008", 3 pgs.
"U.S. Appl. No. 11/129,050, Examiner Interview Summary mailed Feb. 11, 2009", 2 pgs.

(56) References Cited

OTHER PUBLICATIONS

"U.S. Appl. No. 11/129,050, Final Office Action mailed Apr. 21, 2009", 10 pgs.
"U.S. Appl. No. 11/129,050, Final Office Action mailed May 12, 2008", 8 pgs.
"U.S. Appl. No. 11/129,050, Non Final Office Action mailed Nov. 6, 2008", 7 pgs.
"U.S. Appl. No. 11/129,050, Non Final Office Action mailed Nov. 26, 2007", 7 pgs.
"U.S. Appl. No. 11/129,050, Notice of Allowance mailed Apr. 1, 2010", 6 pgs.
"U.S. Appl. No. 11/129,050, Notice of Allowance mailed Jul. 16, 2010", 4 pgs.
"U.S. Appl. No. 11/129,050, Notice of Allowance mailed Aug. 24, 2009", 7 pgs.
"U.S. Appl. No. 11/129,050, Notice of Allowance mailed Nov. 1, 2010", 6 pgs.
"U.S. Appl. No. 11/129,050, Notice of Allowance mailed Dec. 2, 2009", 4 pgs.
"U.S. Appl. No. 11/129,050, Response filed Feb. 23, 2009 to Non Final Office Action mailed Nov. 6, 2008", 13 pgs.
"U.S. Appl. No. 11/129,050, Response filed Feb. 26, 2008 to Non Final Office Action mailed Nov. 26, 2007", 14 pgs.
"U.S. Appl. No. 11/129,050, Response filed Jun. 22, 2009 to Final Office Action mailed Apr. 21, 2009", 9 pgs.
"U.S. Appl. No. 11/129,050, Response filed Jul. 14, 2008 to Final Office Action mailed May 12, 2008", 13 pgs.
"U.S. Appl. No. 11/129,050, Response filed Sep. 28, 2007 to Restriction Requirement mailed Aug. 1, 2007", 11 pgs.
"U.S. Appl. No. 11/129,050, Restriction Requirement mailed Aug. 1, 2007", 6 pgs.
"U.S. Appl. No. 11/129,050, Supplemental Response filed Sep. 12, 2008 to Final Office Action mailed May 12, 2008", 12 pgs.
"U.S. Appl. No. 11/135,985, Examiner Interview Summary mailed Jan. 22, 2008", 3 pgs.
"U.S. Appl. No. 11/135,985, Non-Final Office Action mailed Sep. 25, 2007", 11 pgs.
"U.S. Appl. No. 11/135,985, Notice of Allowance mailed Apr. 25, 2008", 4 pgs.
"U.S. Appl. No. 11/135,985, Preliminary Amendment filed May 24, 2005", 7 pgs.
"U.S. Appl. No. 11/135,985, Response filed Jan. 25, 2008 to Non Final Office Action mailed Sep. 25, 2007", 12 pgs.
"U.S. Appl. No. 11/135,985, Supplemental Preliminary Amendment filed Jan. 17, 2007", 7 pgs.
"U.S. Appl. No. 11/148,107, Examiner Interview Summary mailed Oct. 9, 2008", 4 pgs.
"U.S. Appl. No. 11/148,107, Final Office Action mailed Jan. 14, 2009", 9 pgs.
"U.S. Appl. No. 11/148,107, Non-Final Office Action mailed Jul. 18, 2008", 7 pgs.
"U.S. Appl. No. 11/148,107, Non-Final Office Action mailed Jul. 18 2008", 8 pgs.
"U.S. Appl. No. 11/148,107, Notice of Allowance mailed Feb. 1, 2010", 4 pgs.
"U.S. Appl. No. 11/148,107, Notice of Allowance mailed Mar. 30, 2009", 4 pgs.
"U.S. Appl. No. 11/148,107, Notice of Allowance mailed Aug. 24, 2009", 4 pgs.
"U.S. Appl. No. 11/148,107, Notice of Allowance mailed Nov. 23, 2010", 6 pgs.
"U.S. Appl. No. 11/148,107, Response filed Mar. 16, 2009 to Final Office Action mailed Jan. 14, 2009", 9 pgs.
"U.S. Appl. No. 11/148,107, Response filed Jun. 30, 2008 to Restriction Requirement mailed May 30, 2008", 7 pgs.
"U.S. Appl. No. 11/148,107, Response filed Oct. 20, 2008 to Non-Final Office Action mailed Jul. 18, 2008", 9 pgs.
"U.S. Appl. No. 11/148,107, Restriction Requirement mailed May 30, 2008", 6 pgs.
"U.S. Appl. No. 11/207,251, Final Office Action mailed Feb. 3, 2009", 9 pgs.
"U.S. Appl. No. 11/207,251, Non-Final Office Action mailed Jun. 27, 2008", 8 pgs.
"U.S. Appl. No. 11/207,251, Notice of Allowance mailed May 28, 2009", 4 pgs.
"U.S. Appl. No. 11/207,251, Notice of Allowance mailed Sep. 28, 2009", 4 pgs.
"U.S. Appl. No. 11/207,251, Response filed Apr. 7, 2009 to Final Office Action mailed Feb. 3, 2009", 11 pgs.
"U.S. Appl. No. 11/207,251, Response filed Sep. 29, 2008 to Non Final Office Action mailed Jun. 27, 2008", 14 pgs.
"U.S. Appl. No. 11/275,800, Examiner Interview Summary mailed Aug. 8, 2008", 5 pgs.
"U.S. Appl. No. 11/275,800, Final Office Action mailed Dec. 11, 2008", 10 pgs.
"U.S. Appl. No. 11/275,800, Non-Final Office Action mailed May 2, 2008", 12 pgs.
"U.S. Appl. No. 11/275,800, Response filed Feb. 11, 2009 to Non Final Office Action mailed Dec. 11, 2008", 14 pgs.
"U.S. Appl. No. 11/275,800, Response filed Aug. 29, 2008 to Non-Final Office Action mailed May 2, 2008", 13 pgs.
"U.S. Appl. No. 11/276,735, Examiner Interview Summary mailed Aug. 5, 2009", 4 pgs.
"U.S. Appl. No. 11/276,735, Non Final Office Action mailed May 7, 2009", 8 pgs.
"U.S. Appl. No. 11/276,735, Notice of Allowance mailed Dec. 29, 2009", 6.
"U.S. Appl. No. 11/276,735, Response and Preliminary Amendment filed Feb. 9, 2009 to Restriction Requirement mailed Dec. 8, 2008", 12 pgs.
"U.S. Appl. No. 11/276,735, Response filed Aug. 7, 2009 to Non Final Office Action mailed May 7, 2009", 18 pgs.
"U.S. Appl. No. 11/276,735, Restriction Requirement mailed Dec. 8, 2008", 7 pgs.
"U.S. Appl. No. 11/277,773, Response filed Jul. 21, 2009 to Non Final Office Action mailed Apr. 21, 2009", 9 pgs.
"U.S. Appl. No. 11/277,773, Response filed Oct. 27, 2008 to Non-Final Office Action mailed Jun. 25, 2008", 15 pgs.
"U.S. Appl. No. 11/277,773, Restriction Requirement mailed May 2, 2008", 6 pgs.
"U.S. Appl. No. 11/287,978, Examiner Interview Summary mailed Jan. 25, 2010", 3 pgs.
"U.S. Appl. No. 11/287,978, Final Office Action mailed Jul. 21, 2010", 6 pgs.
"U.S. Appl. No. 11/287,978, Non-Final Office Action mailed Jun. 26, 2009", 7 pgs.
"U.S. Appl. No. 11/287,978, Notice of Allowance mailed Sep. 19, 2011", 7 pgs.
"U.S. Appl. No. 11/287,978, Response filed Sep. 16, 2010 to Final Office Action mailed Jul. 21, 2010", 15 pgs.
"U.S. Appl. No. 11/287,978, Response filed Sep. 28, 2009 to Non Final Office Action mailed Jun. 26, 2009", 10 pgs.
"U.S. Appl. No. 11/382,849, Response filed Apr. 26, 2010 to Final Office Action mailed Jan. 28, 2010", 10 pgs.
"U.S. Appl. No. 11/426,835, Notice of Allowance mailed Apr. 6, 2011", 13 pgs.
"U.S. Appl. No. 11/426,835, Response filed Feb. 14, 2011 to Final Office Action mailed Nov. 12, 2010", 15 pgs.
"U.S. Appl. No. 11/465,878, Issue Notification mailed Jun. 15, 2012", 1 pg.
"U.S. Appl. No. 11/625,003, Examiner Interview Summary mailed Nov. 4, 2009", 4 pgs.
"U.S. Appl. No. 11/625,003, Notice of Allowance mailed Feb. 1, 2010", 6 pgs.
"U.S. Appl. No. 11/777,739, Examiner Interview Summary mailed Feb. 29, 2012", 1 pgs.
"U.S. Appl. No. 12/283,760, Notice of Allowance mailed Jul. 25, 2012", 5 pgs.
"U.S. Appl. No. 12/283,760, Response filed Jul. 17, 2012 to Final Office Action mailed Apr. 24, 2012", 12 pgs.
"U.S. Appl. No. 12/319,642, Notice of Allowance mailed Apr. 13, 2011", 5 pgs.

(56) References Cited

OTHER PUBLICATIONS

"U.S. Appl. No. 12/319,642, Response filed Mar. 21, 2011 to Non Final Office Action mailed Dec. 21, 2010", 14 pgs.
"U.S. Appl. No. 12/510,962, Response filed Mar. 28, 2011 to Non Final Office Action mailed Dec. 28, 2011", 10 pgs.
"U.S. Appl. No. 12/776,557, Corrected Notice of Allowability mailed Jul. 12, 2012", 4 pgs.
"U.S. Appl. No. 13/325,654, Final Office Action mailed Sep. 12, 2013", 12 pgs.
"U.S. Appl. No. 13/325,654, Non Final Office Action mailed Dec. 26, 2012", 10 pgs.
"U.S. Appl. No. 13/325,654, Response filed Feb. 13, 2013 to Non Final Office Action mailed Dec. 26, 2012", 8 pgs.
"U.S. Appl. No. 13/325,654, Restriction Requirement mailed Nov. 9, 2012", 7 pgs.
"U.S. Appl. No. 13/708,196, Examiner Interview Summary mailed Aug. 9, 2013", 3 pgs.
"U.S. Appl. No. 13/708,196, Response filed Aug. 6, 2013 to Non Final Office Action mailed May 8, 2013", 13 pgs.
"U.S. Appl. No. 13/933,937, Non Final Office Action mailed Sep. 26, 2013", 9 pgs.
"BioZ(r) ICG Module", [Online]. Retrieved from the Internet: <URL: http://web.archive.org/web/20010701105207/http://www.cardiodynamics.com/cdprod50.html>, (archived on Jul. 1, 2001), 1 page.
"BioZ.com(tm) Noninvasive Hemodynamic Monitor", [Online]. Retrieved from the Internet: <URL: http://web/archive.org/web/20000617081457/http://www.cardiodynamics.com/cdprod10.html>, (archived Jun. 17, 2000), 2 pages.
"CardioDynamics BioZtect ICG Sensor & Cable System", [Online]. Retrieved from the Internet: <URL: http://web.archive.org/web/200107011105810/http://www.cardiodynamics.com/cdprod60.html>, (archived Jul. 1, 2001), 2 pages.
"CardioDynamics Company Overview", [Online]. Retrieved from the Internet: <URL: http://web.archive.org/web/20001121133300/http://www.cardiodynamics.com/cdcomp10.html>, (archived Nov. 21, 2000), 2 pages.
"European Application Serial No. 03800278.8, Communication dated Oct. 17, 2007", 4 pgs.
"European Application Serial No. 03800278.8, Response filed Feb. 18, 2008 to Communication dated Oct. 17, 2007", 14 pgs.
"European Application Serial No. 06718817.7, Communication dated Nov. 15, 2007", 2 pgs.
"European Application Serial No. 06718817.7, Office Action mailed Apr. 9, 2010", 4 pgs.
"European Application Serial No. 06718817.7, Response filed Mar. 25, 2008 to Communication dated Nov. 15, 2007", 16 pgs.
"European Application Serial No. 06718817.7, Response filed Aug. 19, 2010 to Office Action mailed Apr. 9, 2010", 11 pgs.
"European Application Serial No. 06752527.9, Communication mailed Mar. 8, 2010", 6 pgs.
"European Application Serial No. 06752527.9, Response filed Jul. 7, 2010 to Office Action dated Mar. 8, 2010", 15 pgs.
"European Application Serial No. 06752527.9, Summons to Attend Oral Proceedings Received mailed Jul. 23, 2010", 3 pgs.
"European Application Serial No. 06762527.9, Communication pursuant to Rules 161 to 182 EPC mailed Mar. 3, 2008", 2 pgs.
"European Application Serial No. 06762527.9, Response filed Apr. 9, 2008 to Communication pursuant to Rules 161 to 182 EPC mailed Mar. 3, 2008", 6 pgs.
"European Application Serial No. 06770836.2, Office Action mailed—May 20, 2009", 3 pgs.
"European Application Serial No. 07797336.0, Communication mailed Mar. 10, 2010", 3 pgs.
"European Application Serial No. 07797336.0, Response filed Jul. 6, 2009 to Communication mailed Feb. 24, 2009", 20 pgs.
"European Application Serial No. 07797336.0, Response filed Jul. 7, 2010 to Office Action dated Mar. 10, 2010", 5 pgs.
"European Application Serial No. 07862948.2, Response filed Apr. 30, 2012 to Office Action mailed Dec. 19, 2011", 19 pgs.
"European Application Serial No. 10158651.9, Examination Notification Art. 94(3) mailed Jul. 20, 2011", 5 pgs.
"European Application Serial No. 10158651.9, Extended European Search Report mailed Jul. 29, 2010", 6 pgs.
"European Application Serial No. 10158651.9, Response filed Feb. 28, 2011 to Office Action mailed Sep. 6, 2010", 2 pgs.
"European Application Serial No. 10158651.9, Response filed Nov. 29, 2011 to Office Action mailed Jul. 20, 2011", 10 pgs.
"European Application Serial No. 10173334.3, Examination Notification Art. 94(3) mailed Aug. 24, 2011", 4 pgs.
"European Application Serial No. 10173334.3, Extended European Search Report mailed Oct. 15, 2010", 10 pgs.
"European Application Serial No. 10173334.3, Office Action Response mailed Jan. 2, 2012", 10 pgs.
"European Application Serial No. 10173334.3, Response filed May 23, 2011 to Office Action mailed Nov. 29, 2010", 8 pgs.
"International Application Serial No. PCT/US2003/041481, International Search Report mailed Jun. 4, 2004", 7 pgs.
"International Application Serial No. PCT/US2005/006984, International Search Report mailed Aug. 4, 2005", 13 pgs.
"International Application Serial No. PCT/US2006/001801, International Search Report and Written Opinion mailed Jun. 16, 2006", 12 pgs.
"International Application Serial No. PCT/US2006/018497, International Search Report mailed Oct. 24, 2006", 5 pgs.
"International Application Serial No. PCT/US2006/018497, Written Opinion mailed Oct. 24, 2006", 7 pgs.
"International Application Serial No. PCT/US2006/018642, International Search Report mailed Oct. 24, 2006", 5 pgs.
"International Application Serial No. PCT/US2006/018642, Written Opinion mailed Oct. 24, 2006", 7 pgs.
"International Application Serial No. PCT/US2006/019729, International Search Report and Written Opinion mailed Nov. 17, 2006", 11 pgs.
"International Application Serial No. PCT/US2007/006345, International Search Report mailed Oct. 24, 2007", 6 pgs.
"International Application Serial No. PCT/US2007/006345, Written Opinion mailed Oct. 24, 2007", 8 pgs.
"International Application Serial No. PCT/US2007/068217, International Search Report mailed Oct. 30, 2007", 5 pgs.
"International Application Serial No. PCT/US2007/068217, Written Opinion mailed Oct. 30, 2007", 8 pgs.
"Japanese Application Serial No. 2004-565783, Amendment and Argument filed Feb. 5, 2010 to Office Action Mailed Nov. 11, 2009", (w/ English Translation of Amended Claims), 14 pgs.
"Japanese Application Serial No. 2004-565783, Notice of Allowance mailed Aug. 9, 2010", (W/ English Translation), 4 pgs.
"Japanese Application Serial No. 2004-565783, Office Action mailed Mar. 11, 2010", (W/ English Translation), 8 pgs.
"Japanese application Serial No. 2004-565783, Office Action mailed Nov. 11, 2009", (W/ English Translation), 4 pgs.
"Japanese Application Serial No. 2007-522593, Notice of Allowance mailed Jun. 28, 2011", (W/ English Translation), 6 pgs.
"Japanese Application Serial No. 2007-522593, Response filed Jun. 1, 2011 to Non Final Office Action mailed Dec. 27, 2010", (w/ English Translation of Amended Claims), 31 pgs.
"Japanese Application Serial No. 2007-527615, Office Action mailed May 23, 2011", (W/ English Translation), 9 pgs.
"Japanese Application Serial No. 2007-533593, Office Action mailed Dec. 27, 2010", (w/ English Translation), 4 pgs.
"Japanese Application Serial No. 2007-551478, Office Action mailed Apr. 16, 2012", (W English Translation), 6 pgs.
"Japanese Application Serial No. 2007-551478, Office Action mailed Aug. 31, 2011", (w/ Partial English Translation), 5 pgs.
"Japanese Application Serial No. 2007-551478, Response filed Nov. 29, 2011 to Office Action mailed Aug. 3, 2011", (W/ English Translation), 12 pgs.
"Japanese Application Serial No. 2008-511421, Office Action mailed Nov. 16, 2011", (w/ English Translation), 5 pgs.
"Japanese Application Serial No. 2008-511421, Response filed Mar. 14, 2012 to Office Action mailed Nov. 16, 2011", (w/ English Translation of Amended Claims), 16 pgs.

(56) References Cited

OTHER PUBLICATIONS

"Japanese Application Serial No. 2008-511421, Voluntary Amendment filed Apr. 27, 2009", (W/ English Translation of Amended Claims), 11 pgs.
"Japanese Application Serial No. 2008-513587, Office Action mailed Jan. 23, 2012", (English Translation), 4 pgs.
"Japanese Application Serial No. 2008-513587, Response filed Apr. 23, 2012 to Office Action mailed Jan. 23, 2012", (W/ English Translation), 5 pgs.
"Japanese Application Serial No. 2009-502827, Office Action mailed Jul. 2, 2012", (W/ English Translation), 6 pgs.
"Japanese Application Serial No. 2009-502827, Office Action mailed Jul. 19, 2012", (W/ English Translation), 6 pgs.
"Japanese Application Serial No. 2009-502827, Response filed Apr. 27, 2012 to Office Action mailed Feb. 8, 2012", (W/ English Translation of Claims), 30 pgs.
"Japanese Application Serial No. 2009-502827, Response filed Sep. 24, 2012 to Office Action mailed Jul. 19, 2012", (W/ English Translation of Claims), 9 pgs.
"Japanese Application Serial No. 2009-509916, Office Action mailed Feb. 8, 2012", (W/ English Translation), 5 pgs.
"Japanese Application Serial No. 2009-509916, Response filed May 2, 2012 to Office Action mailed Mar. 6, 2012", (W/ English Translation of Claims), 12 pgs.
"Japanese Application Serial No. 2009-510093, Office Action mailed Mar. 12, 2012", (w/ English Translation), 9 pgs.
"Japanese Application Serial No. 2009-510093, Response filed Jun. 11, 2012 to Office Action mailed Mar. 12, 2012", (W/ English Translation of Claims), 11 pgs.
"Overview of Impedance Cardiography (ICG)", [Online]. Retrieved from the Internet: <URL: http:/web.archive.org/web/20021003000713/http://www.impedancecariography.com/icgover10.html>, (archived Oct. 3, 2002), 5 Pages.
Aaron, S. D, et al., "How accurate is spirometry at predicting restrictive pulmonary impairment?", Chest, 115(3), (Mar. 1999), 869-73.
Abrams, Jonathan, "Current Concepts of the Genesis of Heart Sounds", JAMA 239(26), (Jun. 30, 1978), 3 pgs.
Adolph, R. J., et al., "The clinical value of frequency analysis of the first heart sound in myocardial infarction.", Circulation, 41(6), (Jun. 1970), 1003-14.
Amende, I., "Hemodynamics in ischemia: diastolic phase", Z. Kardiol., 73 Suppl 2, [Article in German With English Abstract], (1984), 127-33.
Auricchio, A., et al., "Cardiac Resynchronization Therapy Restores Optimal Atrioventricular Mechanical Timing in Heart Failure Patients with Ventricular Conduction Delay", Journal of the American College of Cardiology, 39(7), (2002), 1163-1169.
Auricchio, Angelo, et al., "Dynamically Optimized Multisite Resynchronizer", U.S. Appl. No. 10/071,875, filed Feb. 8, 2002, 22 pgs.
Barbaro, V., et al., "A portable unit for remote monitoring of pacemaker patients", Journal of Telemedicine and Telecare, 3(2), (1997), 96-102.
Baynham, Tamara C, "Method and Apparatus for Cardiac Protection Pacing", U.S. Appl. No. 11/129,050, filed May 13, 2005, 33 pgs.
Birnbaum, Y, et al., "Ischemic preconditioning at a distance: reduction of myocardial infarct size by partial reduction of blood supply combined with rapid stimulation of the gastrocnemius muscle in the rabbit.", Circulation, 96(5), (Sep. 7, 1997), 1641-6.
Breithardt, O A, et al., "Acute effects of cardiac resynchronization therapy on functional mitrel regurgitation in advanced systolic heart failure", Journal of the American College of Cardiology, 41(5), (May 21, 2003), 765-70.
Brockway, Marina, et al., "Method and Apparatus for Monitoring Heart Failure Patients With Cardiopulmonary Comorbidities", U.S. Appl. No. 10/897,856, filed Jul. 23, 2004, 54 pgs.
Brockway, Marina, et al., "Method and Apparatus for Optimization of Cardiac Resynchronization Therapy Using Heart Sounds", U.S. Appl. No. 10/865,498, filed Jun. 10, 2004, 45 pgs.

Carabello, B A, "Mitrel valve disease", Current Problems in Cardiology,18(7), (Jul. 1993), 423-78.
Carlson, Gerrard M, et al., "Hemodynamic Stability Assessment Based on Heart Sounds", U.S. Appl. No. 11/277,773, filed Mar. 29, 2006, 39 pgs.
Carr, William N., "Integrated Pressure Sensor With Remote Power Source and Remote Readout", The 8th International Conference on Solid-State Sensors and Actuators and Eurosensors IX, Digest of Technical Papers, Stockholm, Sweden, (Jun. 25-29, 1995), 624-627.
Clarke, W. B., et al., "Spectral energy of the first heart sound in acute myocardial ischemia. A correlation with electrocardiographic, hemodynamic, and wall motion abnormalities.", Circulation, 57(3), (Mar. 1978), 593-8.
Collins, Sean, "Diagnostic Utility of an S3 in Dyspneic ED Patients", Inovise Medical Inc, University of Cincinnati Medical Center, (2005), 6 Pages.
Del Rio, C. L., et al., "Use of Myocardial Electrical Impedance to Assess the Efficacy of Preconditioning", IEEE Computers in Cardiology, (2002), 489-492.
Ding, Jiang, et al., "Cardiac Pacing Using Adjustable Atrio-Ventricular Delays", U.S. Appl. No. 10/008,830, filed Dec. 7, 2001, 1-42.
Ding, Jiang, et al., "Cardiac Pacing Using Adjustable Atrio-Ventricular Delays", U.S. Appl. No. 10/243,811 mailed Sep. 13, 2002, 1-39.
Dzwonczyk, R., et al., "Myocardial electrical impedance responds to ischemia and reperfusion in humans", IEEE Transactions on Biomedical Engineering, 51(12), (Dec. 2004), 2206-2209.
Fenster, M S, et al., "Mitral regurgitation: an overview", Curr Probl Cardiol., 20(4), (Apr. 1995), 193-280.
Girouard, Steven D, et al., "Cardiac Rhythm Management Systems and Methods Predicting Congestive Heart Failure Status", U.S. Appl. No. 10/213,268, filed Aug. 6, 2002, 33 pgs.
Hada, Yoshiyuki, et al., "Pulsus alternans determined by biventricular simultaneous systolic time intervals", Circulation, 65(3), (Mar. 1982), 617-26.
Haro, Carlos, et al., "Respiration-Synchronized Heart Sound Trending", U.S. Appl. No. 11/561,428, filed Nov. 20, 2006, 54 pgs.
Hatlestad, J. D, et al., "Physiological Response to Posture Change", U.S. Appl. No. 11/466,925, filed Aug. 24, 2006, 21 pgs.
Hatlestad, John, "Methods and Devices for Detection of Context When Addressing a Medical Condition of a Patient", U.S. Appl. No. 10/269,611, filed Oct. 11, 2002, 29 pgs.
Henriques, Jose P., et al., "Outcome of primary angioplasty for acute myocardial infarction during routine duty hours versus during off-hours", J Am Coll Cardiol, 41(12), (Jun. 18, 2003), 2138-2142.
Hsu, William, "System and Method for Classifying Tachycardia Arrhythmias Having 1:1 Atrial to Ventricular Rhythms", U.S. Appl. No. 09/417,588, filed Oct. 13, 1999, 39 pgs.
Hughes, Howard C, et al., "The Effects of Electrode Position on the Detection of the Transvenous Cardiac Electrogram", PACE, vol. 3, (Nov.-Dec. 1980), 651-655.
Hutten, H., et al., "Cardiac pacemaker as bridge to cardiac telemonitoring", Biomedizinische Technik, 41(6), Institut for Elektro-und Biomedizinische Technik Technische Universitat Graz., [Article in German With English Abstract], (Jun. 1996), 158-165.
Hutten, H., et al., "Cardiac Telemonitoring through the Linkage of Close-up Telemetry and Internet Transmission", Institute for Electro- and Biomedical Technology, Technical University of Graz Inffeldgasse, 42, [Article in German with English Abstract], (1997), 67-69.
Ji, J., "An Ultraminiature CMOS Pressure Sensor for a Multiplexed Cardiovascular Catheter", IEEE Transactions on Electron Devices, vol. 39, No. 10, (Oct. 1992), pp. 2260-2267.
Kadhiresan, Veerichetty, et al., "Cardiopulmonary Functional Status Assessment Via Heart Rate Response Dectection by Implantable Cardiac Device", U.S. Appl. No. 10/914,632, filed Aug. 9, 2004, 18 pgs.
Kameli, Nader, "Integrated System for Managing Patients With Heart Failure", U.S. Appl. No. 11/553,103, filed Oct. 26, 2006, 41 pgs.
Kenknight, Bruce H, et al., "Method and Apparatus for Establishing Context Among Events and Optimizing Implanted Medical Device Performance", U.S. Appl. No. 10/093,353, filed Mar. 6, 2002, 43 pgs.

(56) References Cited

OTHER PUBLICATIONS

Kis, A., "Repeated cardiac pacing extends the time during which canine hearts are protected against ischaemia-induced arrhythmias : role of nitric oxide.", Journal of Molecular and Cellular Cardiology, 31(6), (Jun. 1999), 1229-1241.

Kis, A., et al., "Repeated Cardiac Pacing Extends the Time During Which Canine Hearts are Protected Against Ischaemia-induced Arrhythmias: Role of Nitric Oxide", Journal of Molecular and Cellular, 31(6), (1999), 1229-1241.

Konta, Tsuyoshi, et al., "Significance of Discordant ST Alternans in Ventricular Fibrillation", Circulation, 82(6), (Dec. 1990), 2185-2189.

Krayenbuhl, H. P., "Hemodynamics in ischemia. Systolic phase", Z. Kardiol., 73 Suppl 2, [Article in German with English Abstract], (1984), 119-25.

Leitch, James, et al., "Feasibility of an implantable arrhythmia monitor", PACE, vol. 15, No. 12, (Dec. 1992), 2232-5.

Lincoln, William C., "Classifying Tachyarrhythmia Using Time Interval Between Ventricular Depolarization and Mitral Valve Closure", U.S. Appl. No. 10/618,261, filed Jul. 11, 2003, 26 pgs.

Loukogeorgakis, S. P., et al., "Remote ischemic preconditioning provides early and late protection against endothelial ischemia-reperfusion injury in humans: role of the autonomic nervous system. ", J Am Coll Cardiol., 46(3), (Aug. 2, 2005), 450-6.

Maile, Keith R., et al., "A Dual-Use Sensor for Rate Responsive Pacing and Heart Sound Monitoring", U.S. Appl. No. 10/703,175, filed Nov. 6, 2003, 41 pgs.

Maile, Keith R., et al., "Determining a Patient's Posture From Mechanical Vibrations of the Heart", U.S. Appl. No. 10/900,570, filed Jul. 28, 2004, 24 pgs.

Mazur, Alexander, "Functional similarity between electrograms recorded from an implantable cardioverter defibrillator emulator and the surface electrocardiogram", PACE, vol. 24, (Jan. 2001), 34-40.

McCabe, Aaron, "Self-Diagnostic Method and System for Implantable Cardiac Device", U.S. Appl. No. 10/890,810, filed Jul. 14, 2004, 18 pgs.

Melo, L. G., et al., "Molecular and cell-based therapies for protection, rescue, and repair of ischemic myocardium: reasons for cautious optimism.", Circulation, 109(20), (May 2004), 2386-93.

Min, Mart, "Electrical Impedance and Cardiac Monitoring-Technology, Potential and Applications", International Journal of Bioelectromagnetism, 5(1), (2003), 53-56.

Mower, Morton, "Method and Apparatus for Treating Hemodynamic Disfunction".

Nesto, R. W., et al., "The ischemic cascade: temporal sequence of hemodynamic, electrocardiographic and symptomatic expressions of ischemia.", American Journal of Cardiology, 59(7), (Mar. 9, 1987), 23C-30C.

Obaidat, M. S., et al., "Performance of the short-time Fourier transform and wavelet transform to phonocardiogram signal analysis", Database Inspec [Online] The Institution of Electrical Engineers, Stevenage, GB, (1992), 1 pg.

Ostadal, Petr, et al., "The effect of early treatment by cerivastatin on the serum level of C-reactive protein, interleukin-6, and interleukin-8 in patients with unstable angina and non-Q-wave myocardial infarction", Molecular and Cellular Biochemistry, 246, (2003), 45-50.

Palomo, A R, et al., "Echo-phonocardiographics determination of left atrial and left ventrical filling pressures with and without mitral stenosis", Circulation, vol. 61, No. 5, (May 1980), 1043-1047.

Panju, Akbar A, et al., "Is This Patient Having a Myocardial Infraction?", JAMA, 280(14), (Oct. 14, 1998), 1256-1263.

Paolocci, Nazareno, et al., "Positive inotropic and lusitropic effects of HNO/NO—in failing hearts: Independence from beta-adrenergic signaling", Proceedings of the National Academy of Sciences USA, 100(9), (Apr. 29, 2003), 5537-5542.

Pastore, Joseph M, et al., "Method and Apparatus for Detecting Acoustic Oscillations in Cardiac Rythm", U.S. Appl. No. 10/138,046, filed May 3, 2002, 25 pgs.

Pastore, Joseph M, "Method and Apparatus for Detecting Oscillations in Cardiac Rhythm", U.S. Appl. No. 10/172,825, filed Jun. 14, 2002, 33 pgs.

Patangay, Ahilash, et al., "Ischemia Detection Using Heart Sound Timing", U.S. Appl. No. 11/625,003, filed Jan. 19, 2007, 69 pgs.

Pinchak, Alfred C, et al., "Multiaxial Accelerometers", Encyclopedia of Medical Devices and Instrumentation, vol. 1, Department of Electrical and Computer Engineering, (1988), 11 Pages.

Ponikowski, P., et al., "Oscillatory Implications and Role of Augmented Peripheral Chemosensitivity", Circulation, 100, (1999), 2418-2424.

Prinzen, Frits W, "Mapping of regional myocardial strain and work during ventricular pacing: experimental study using magnetic resonance imaging tagging", Journal of the American College of Cardiology, 33(6), (May 1999), 1735-1742.

Ritter, P., et al., "A Built-In System Based on the Peak Endocardial Acceleration (PEA) for AV-Delay Optimization in DDDR Pacing", PACE, 20(5) (Part II), (Abstract of Paper presented at Europace '97), (May 1997), 1567.

Rohling, H., "Radar CFAR Thresholding in Clutter and Multiple Target Situations", IEEE Trans. Aerosp. Electron. Syst., vol. AES-19, No. 4, (Jul. 1983), 608-621.

Rohling, H., "Some radar topics: waveform design, range CFAR and target recognition", NATO Advanced Study Institute, Advances in Sensing with Security Applications, (2005), 1-30.

Rosa, A., et al., "Ectopic Pacing at Physiological Rate Improves Postanoxic Recovery of the Developing Heart", Am. J. Physiol.—Heart Circ. Physiol., 284, (2003), 2384-2392.

Rubenstein, Donald S, et al., "Premature Beats Elicit a Phase Reversal of Mechanoelectrical Alternans in Cat Ventricular Myocytes", Circulation, vol. 91, No. 1, Jan. 1995, American Heart Association, (Jan. 1, 1995), 201-214.

Sakamoto, T., et al., "Hemodynamic determinants of the amplitude of the first heart sound", Circulation Research, 16, (1965), 45-57.

Salerno, D. M., "Seismocardiography for monitoring changes in left ventricular function during ischemia.", Chest, 100(4), (Oct. 1991), 991-3.

Say, O, et al., "Classification of heart sounds by using wavelet transform", 24th Annual Conference and the Annual Fall Meeting of the Biomedical Engineering Society] EMBS/BMES Conference, vol. 1, (2002), 128-129.

Schaefer, Saul, et al., "Clinical and hemodynamic characteristics of patients with inducible pulsus alternans", American Heart Journal, vol. 115, No. 6, (Jun. 1988), 1251-7.

Schoemaker, R. G., et al., "Bradykinin mediates cardiac preconditioning at a distance", Am J Physiol Heart Circ Physiol., 278(5), (May 2000), H1571-6.

Sheiban, I., et al., "Time course and determinants of left ventricular function recovery after primary angioplasty in patients with acute myocardial infarction", J Am Coll Cardiol., 38(2), (Aug. 2001), 464-71.

Siejko, K. Z., et al., "Method for Correction of Posture Dependence on Heart Sounds", U.S. Appl. No. 11/037,275, filed Jan. 18, 2005, 26 pgs.

Siejko, Krzysztof Z., "A Third Heart Sound Activity Index for Heart Failure Monitoring", U.S. Appl. No. 10/746,874, filed Dec. 24, 2003, 41 pgs.

Siejko, Krzysztof Z, et al., "A Third Heart Sound Activity Index for Heart Failure Monitoring", U.S. Appl. No. 11/465,878, filed Aug. 21, 2006, 35 pgs.

Siejko, Krzysztof Z., et al., "Method and Apparatus for Third Heart Sound Detection", U.S. Appl. No. 10/746,853, filed Dec. 24, 2003, 40 pgs.

Siejko, Krzysztof Z, et al., "Physiological Event Detection Systems and Methods", U.S. Appl. No. 11/276,735, filed Mar. 13, 2006, 56 pgs.

Smith, Damon, et al., "Influence of the Aortic Component of the Second Heart Sound on Left Ventricular Maximal Negative dP/dt in the Dog", Am. J. Cardiol., 55: 205, (1985), 205-209.

Smith, R.A., et al., "An intranet database for pacemaker patients", International Journal of Medical Informatics, 47, (1997), 79-82.

(56) References Cited

OTHER PUBLICATIONS

Smith, V., "Systems, Devices and Methods for Tachyarrythmia Discrimination or Therapy Decisions", U.S. Appl. No. 10/897,365, filed Jul. 22, 2004, 38 pgs.
Stahmann, Jeffrey, et al., "Thoracic Impedance Detection With Blood Resistivity Compensation", U.S. Appl. No. 10/921,503, filed Aug. 19, 2004, 38 pgs.
Stein, Emanuel, et al., "Rapid Interpretation of Heart Sounds and Murmurs", Baltimore : Williams & Wilkins, 4th ed., (1997), 85-105.
Theres, Heinz P, et al., "Detection of acute myocardial ischemia during percutaneous transluminal coronary angioplasty by endocardial acceleration.", Pacing Clin Electrophysiol., vol. 27, No. 5, (May 2004), 621-625.
Theres, Heinz, et al., "Electrogram signals recorded from acute and chronic pacemaker implantation sites in pacemaker patie", PACE, vol. 21, Part 1, (Jan. 1998), 11-17.
Theroux, P., et al., "Regional Myocardial function in the conscious dog during acute coronary occlusion and responses to morphine, propranolol, nitroglycerin, and lidocaine.", Circulation, 53(2), (Feb. 1976), 302-14.
Vegh, A, et al., "Transient ischaemia induced by rapid cardiac pacing results in myocardial preconditioning", Cardiovascular Research, 25(12), (Dec. 1991), 1051-3.
Wariar, R., et al., "Systems and Methods for Multi-Axis Cardiac Vibration Measurements", U.S. Appl. No. 11/135,985, filed May 24, 2004, 35 pgs.
Wariar, Ramesh, et al., "Detection of Myocardial Ischemia From the Time Sequence of Implanted Sensor Measurements", U.S. Appl. No. 11/426,835, filed Jun. 27, 2006, 41 pgs.
Watanabe, M., et al., "Developmental Remodeling and Shortening of Cardiac Outflow Tract Involves Myocyte Programmed Cell Death", Development, 125(19), (1998), 3809-3820.
Weissler, A. M., "Systolic time intervals in heart failure in man", Circulation, 37(2), (Feb. 1968), 149-59.
Wood, J. C, et al., "Time-Frequency Transforms: A New Approach to First Heart Sound Frequency Dynamics", IEEE Transactions on Biomedical Engineering, 39 (7), IEEE Service Center, US, (Jul. 1, 1992), 730-740.
Xu, J, et al., "A new, simple, and accurate method for non-invasive estimation of pulmonary arterial pressure", Heart 88, (2002), 76-80.
Yu, Yinghong, et al., "Method and Apparatus for Optimizing Stroke Volume During DDD Resynchronization Therapy Using Adjustable Atrio-Ventricular Delays", U.S. Appl. No. 10/314,899, filed Dec. 9, 2002, 1-50.
Yu, Yinghong, et al., "Method and Apparatus for Optimizing Ventricular Synchrony During DDD Resynchronization Therapy Using Adjustable Atrio-Ventricular Delays", U.S. Appl. No. 10/314,910, filed Dec. 9, 2002, 1-50.
Zanon, F, et al., "Reduced mitral regurgitation in heart failure patients submitted to cardiac resynchronization therapy: a short-term prospective study", Italian Heart Journal, 5(11), (Nov. 2004), 826-30.
Zhang, Y., et al., "Ischemia Detection Using a Heart Sound Sensor", U.S. Appl. No. 11/148,107, filed Jun. 8, 2005, 41 pgs.
Zhao, et al., "Inhibition of myocardial injury by ischemic postconditioning during reperfusion: comparison with ischemic preconditioning", Am J Physiol Heart Circ Physiol, 285(2), (Aug. 2003), H579-H588.
Zhi-Qing, Z., et al., "Inhibition of myocardial injury by ischemic postconditioning during reperfusion: comparision with ischemic preconditioning", Am J Physiol Heart Circ Physiol, 285(2), (2003), H579-H588.
Zhu, Qingsheng, et al., "Method and Apparatus for Determining Changes in Heart Failure Status", U.S. Appl. No. 10/001,223, filed Nov. 15, 2001, 22 pgs.
Zin, Z M, et al., "Wavelet analysis and classification of Mitral regurgitation and normal heart sounds based on artificial neural networks", Seventh International Symposium on Signal Processing and Its Applications, vol. 2, (Jul. 1-4, 2003), 619 -620.
"U.S. Appl. No. 13/708,196 Response filed Dec. 23, 2013 to Final Office action mailed Oct. 23, 2013", 14 pgs.
"U.S. Appl. No. 13/708,196, Advisory Action mailed Jan. 14, 2014", 2 pgs.
"U.S. Appl. No. 13/708,196, Final Office Action mailed Oct. 23, 2013", 10 pgs.
"U.S. Appl. No. 13/708,196, Non Final Office Action mailed Feb. 14, 2014", 9 pgs.

\* cited by examiner

MONITORING OF HEART SOUNDS

RELATED APPLICATION

This application is a continuation of Patangay et al., U.S. patent application Ser. No. 13/491,848, entitled "Monitoring of Heart Sounds" filed on Jun. 8, 2012, now issued as U.S. Pat. No. 8,597,191, which is a continuation of U.S. patent application Ser. No. 11/777,739, now issued as U.S. Pat. No. 8,211,034, filed on Jul. 13, 2007, which is a continuation-in-part of commonly assigned, Haro et al., U.S. patent application Ser. No. 11/561,428, entitled "Respiration-Synchronized Heart Sound Trending," which was filed Nov. 20, 2006, now abandoned, and which are incorporated by reference herein.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable insulin pumps, devices implanted to administer drugs to a patient, or implantable devices with neural stimulation capability.

Heart sounds are associated with mechanical vibrations from activity of a patient's heart and the flow of blood through the heart. Heart sounds recur with each cardiac cycle and are separated and classified according to the activity associated with the vibration. The first heart sound (S1) can be thought of as the vibrational sound made by the heart during tensing of the mitral valve. The second heart sound (S2) can be thought of as marking the beginning of diastole. The third heart sound (S3) and fourth heart sound (S4) can be conceptualized as related to filling pressures of the left ventricle during diastole. Heart sounds are useful indications of proper or improper functioning of a patient's heart.

OVERVIEW

This document relates generally to systems, devices, and methods for monitoring one or more heart sounds. In example 1, a system includes an implantable medical device (IMD). The IMD includes an implantable heart sound sensor circuit configured to produce an electrical heart sound signal representative of a heart sound of a subject and a processor circuit. The processor circuit is coupled to the heart sound sensor circuit and includes a detection circuit, a heart sound feature circuit and a trending circuit. The detection circuit configured to detect a physiologic perturbation and the heart sound feature circuit is configured to identify a heart sound feature in the electrical signal. The processor circuit is configured to trigger the heart sound feature circuit in relation to a detected physiologic perturbation. The trending circuit is configured to trend the heart sound feature in relation to a recurrence of the physiologic perturbation. The processor circuit is configured to declare a change in a physiologic condition of the patient according to the trending.

In example 2, the heart sound feature circuit of example 1 is optionally configured to identify a plurality of candidate heart sound features. The processor circuit optionally includes a ranking circuit configured to rank the candidate heart sound features, and select a heart sound feature for trending according to the ranking.

In example 3, the ranking circuit of example 2 is optionally configured to rank the candidate features according to a physiologic condition of the subject.

In example 4, the IMD of examples 1-4 optionally includes a second implantable sensor circuit in electrical communication with the processor circuit. The implantable sensor circuit is configured to produce a second electrical sensor signal related to one or more physiologic cardiovascular events in the subject. The detection circuit of examples 1-4 is optionally configured to detect the physiologic perturbation from the second electrical sensor signal.

In example 5, the second implantable sensor circuit of example 4 optionally includes a cardiac signal sensing circuit configured to provide an electrical representative of an intrinsic cardiac signal of the subject. The detection circuit is optionally configured to detect a premature ventricular contraction (PVC) to trigger the heart sound feature circuit.

In example 6, the second implantable sensor circuit of example 4 optionally includes an activity sensor to provide a signal representative of a physical activity level of the subject. The detection circuit is optionally configured to detect that a physical activity level of the subject exceeds a threshold activity level from the signal to trigger the heart sound feature circuit.

In example 7, the second implantable sensor circuit of example 4 optionally includes a posture sensor, and the detection circuit is optionally configured to detect a change in posture of the subject to trigger the heart sound feature circuit.

In example 8, the second implantable sensor circuit of example 4 optionally includes a cardiac signal sensing circuit configured to provide an electrical representative of an intrinsic cardiac signal of the subject. The detection circuit is optionally configured to detect that a heart rate of the subject exceeds a threshold heart rate to trigger the heart sound feature circuit.

In example 9, the second implantable sensor circuit of example 4 optionally includes a respiration sensor to provide a signal representative of respiration of the subject. The detection circuit is optionally configured to detect a phase of a respiration cycle of the subject from the signal to trigger the heart sound feature circuit.

In example 10, the processor circuit of examples 1-9 optionally includes a timer circuit, and the processor circuit is optionally configured to trigger the heart sound feature circuit in relation to a time the subject receives a drug therapy.

In example 11, the processor circuit of examples 1-10 optionally includes a timer circuit, and the processor circuit is optionally configured to trigger the heart sound feature circuit in relation to a phase of a circadian cycle of the subject.

In example 12, the IMD of examples 1-11 optionally includes a therapy circuit in electrical communication with the processor circuit. The therapy circuit is configured to provide a therapy to the subject, and the processor circuit is optionally configured to initiate a therapy to cause the physiologic perturbation and to trigger the heart sound feature circuit in a time relation to the therapy.

In example 13, the processor circuit of example 12 is optionally configured to initiate a paced cardiac contraction as the physiologic perturbation and to trigger the heart sound feature circuit in a time relation to the paced cardiac contraction.

In example 14, the processor circuit of examples 12 and 13 is optionally configured to initiate a premature ventricular contraction (PVC) as the physiologic perturbation and to trigger the heart sound feature circuit in a time relation to the PVC.

In example 15, a method includes sensing an electrical heart sound signal representative of a heart sound of a subject in relation to a physiologic perturbation using an IMD, identifying a feature of the heart sound signal, trending the feature of the heart sound signal in relation to a recurrence of the physiologic perturbation, and identifying a change in a physiologic condition of the subject from the trending.

In example 16, identifying the feature of example 15 optionally includes identifying a plurality of candidate features of the heart sound signal, ranking the candidate features, and selecting a feature for trending according to the ranking.

In example 17, ranking the candidate features of example 16 optionally includes ranking the candidate features according to a physiologic condition of the subject.

In example 18, identifying the feature of the heart sound signal of examples 15-17 optionally includes triggering identification of the feature of the heart sound in relation to a detected physiologic perturbation.

In example 19, identifying the feature of the heart sound signal of examples 15-18 optionally includes triggering identification of the feature of the heart sound in relation to an induced physiologic perturbation.

In example 20, the physiologic perturbation of examples 15-19 optionally includes a premature ventricular contraction (PVC), and identifying the feature of the heart sound signal optionally includes sensing a heart sound signal includes sensing a heart sound signal in relation to the PVC.

In example 21, the physiologic perturbation of examples 15-20 optionally includes a change in posture of the subject, and sensing the heart sound signal optionally includes sensing a heart sound signal in relation to the change in posture.

In example 22, the physiologic perturbation of examples 15-21 optionally includes a heart rate of the subject exceeding a threshold heart rate, and sensing the heart sound signal optionally includes sensing a heart sound signal in relation to the heart rate of the subject exceeding the threshold heart rate.

In example 23, the physiologic perturbation of examples 15-22 optionally includes the subject receiving drug therapy, and sensing the heart sound signal optionally includes sensing a heart sound signal in relation to a time the subject receives the drug therapy.

In example 24, the physiologic perturbation of examples 15-23 optionally includes a paced cardiac contraction, and sensing the heart sound signal optionally includes sensing the heart sound signal in relation to the paced cardiac contraction.

In example 25, the physiologic perturbation of examples 15-24 optionally includes a phase of a respiration cycle, and sensing the heart sound signal optionally includes sensing the heart sound signal in relation to the phase of a respiration cycle.

In example 26, the physiologic perturbation of examples 15-25 optionally corresponds to a circadian pattern, and the sensing the heart sound signal optionally includes sensing the heart sound signal in relation to the circadian pattern.

In example 27, the physiologic perturbation of examples 15-26 optionally includes activity of the subject exceeding a threshold activity level, and sensing the heart sound signal optionally includes sensing the heart sound signal in relation to the activity level of the subject exceeding the threshold activity level.

In example 28, a system includes means for implantably sensing an electrical heart sound signal representative of a heart sound of a subject, means for identifying a feature of the heart sound signal in relation to a detected physiologic perturbation, means for trending the feature of the heart sound signal in relation to a recurrence of the physiologic perturbation, and means for identifying a change in a physiologic condition of the subject from the trending.

In example 29, a system example includes an IMD and an external device. The IMD includes an implantable heart sound sensor circuit configured to produce an electrical heart sound signal representative of a heart sound of a subject and a first processor circuit coupled to the heart sound sensor circuit. The processor circuit includes a detection circuit configured to detect a physiologic perturbation; and a heart sound feature circuit configured to identify a heart sound feature in the electrical signal. The processor circuit is configured to trigger the heart sound feature circuit in relation to a detected physiologic perturbation. The external device includes a second processor circuit which includes a trending circuit configured to trend the heart sound feature in relation to a recurrence of the physiologic perturbation. The second processor circuit is configured to declare a change in a physiologic condition of the patient according to the trending.

In example 30, the heart sound feature circuit of example 29 is optionally configured to identify a plurality of candidate heart sound features. The first processor circuit is optionally configured to communicate information about the heart sound signal features to the external device. The second processor circuit optionally includes a ranking circuit configured to rank the candidate heart sound features, and select a heart sound feature for trending according to the ranking.

In example 31, the ranking circuit of example 30 is optionally configured to rank the candidate features according to a physiologic condition of the subject.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Because heart sounds are a mechanical measure of a patient's hemodynamic system, monitoring of one or more heart sounds can aid a caregiver in detecting overall progression of heart disease.

Figure 1:
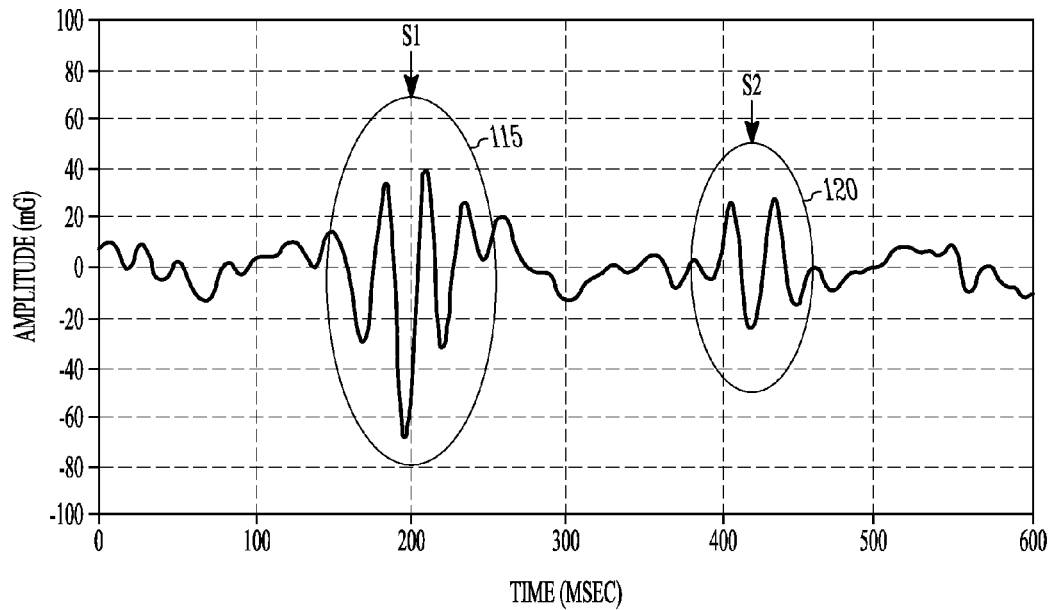
FIG. 1 is an illustration of a graph of S1 and S2 heart sounds.

FIG. 1 is an illustration of a graph of the S1 115 and S2 120 heart sounds. The mechanical events indicated by heart sounds change when there is a physiologic or patho-physiologic change in the cardiovascular system. These changes can be viewed as physiologic perturbations. For example, when a patient exercises, their heart rate and cardiac stroke volume increases. The increase in heart rate decreases the cardiac cycle length and shifts the S1 and S2 heart sounds in time. The increase in stroke volume changes the amplitudes of the S1 and S2 heart sounds. Other examples of such physiologic perturbations include, without limitation, a change in patient posture, one or more premature ventricular contractions (PVCs), drug therapy received by the patient, a paced cardiac contraction, and the inhaling or exhaling of the patient. A specific perturbation causes an expected change in the heart sounds. Monitoring heart sounds when the specific perturbation occurs may provide additional information about the physiologic condition of the patient or subject.

Figure 2:
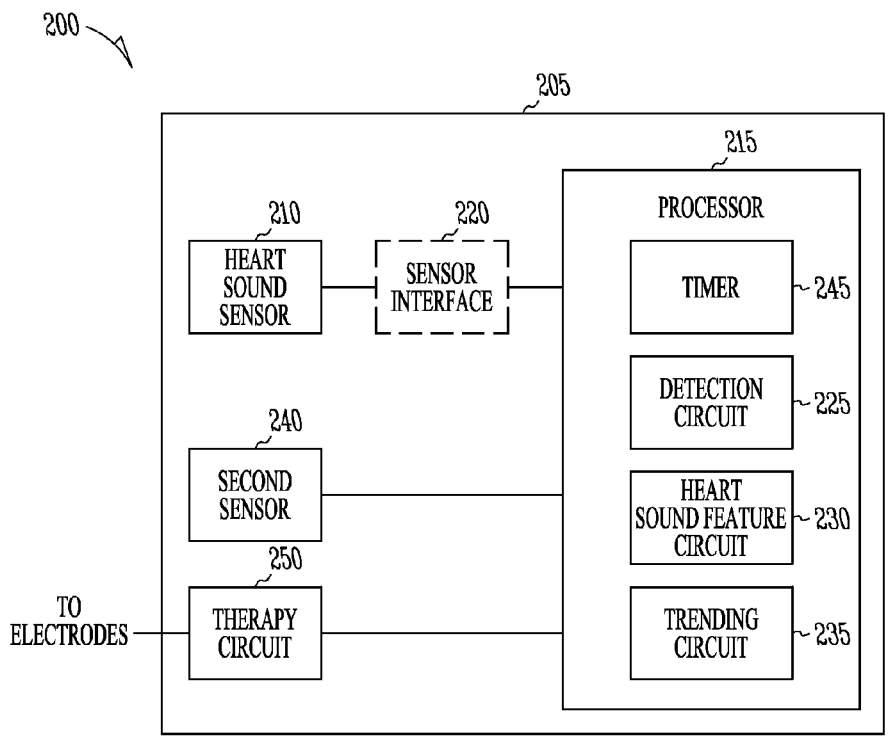
FIG. 2 shows a block diagram of portions of an example of a system for monitoring one or more heart sounds.

FIG. 2 shows a block diagram of portions of an example of a system 200 for monitoring one or more heart sounds. The system 200 includes an implantable medical device (IMD) 205 that in turn includes a heart sound sensor circuit 210. Heart sound sensors generally include implantable acoustic sensors that convert the detected sounds of the heart into an electrical signal representative of the heart sounds. In some examples, the heart sound sensor circuit 210 includes an accelerometer located within a hermetically sealed canister or "can" of the IMD 205. In another sensor example, a microphone is located within the IMD can. In another example, the heart sound sensor circuit 210 includes a strain gauge.

The system 200 also includes a processor circuit 215 coupled to the heart sound sensor circuit 210. In some examples, the processor circuit 215 is coupled to the heart sound sensor circuit 210 through a heart sound sensor interface circuit 220. The heart sound sensor interface circuit 220 provides signal conditioning such as signal filtering and/or amplification for example.

The processor circuit 215 includes a detection circuit 225, a heart sound feature circuit 230, and a trending circuit 235. The processor circuit 215 can be implemented using hardware circuits, firmware, software or any combination of hardware, firmware and software. Examples, include a microprocessor, a logical state machine, and a processor such as a microprocessor, application specific integrated circuit (ASIC), or other type of processor. The processor circuit 215 is configured to perform or execute a function or functions. Such functions correspond to circuits or other type of modules, which are software, hardware, firmware or any combination thereof. Multiple functions may be performed in one or more of the circuits.

The detection circuit 225 detects a physiologic perturbation. When a perturbation is detected, the processor circuit 215 triggers the heart sound feature circuit 230 in relation to the perturbation to identify a heart sound feature in the electrical signal representative of the heart sound.

In some examples, the detection circuit 225 detects the physiologic perturbation using the electrical signal from the heart sound sensor circuit 210. For example, if the physiologic perturbation is patient exercise, the detection circuit 225 may detect exercise from a shift in S1 and S2 heart sounds. If the heart sound sensor circuit 210 includes an accelerometer, the accelerometer may double as an activity sensor and the detection circuit 225 may detect patient activity such as exercise using the accelerometer. Descriptions of systems to monitor heart and detect patient activity may be found in Maile et al., U.S. Patent Application Publication No. 20050102001, entitled "Dual-Use Sensor for Rate Responsive Pacing and Heart Sound Monitoring, filed Nov. 6, 2003, now issued as U.S. Pat. No. 7,248,923, which is incorporated herein by reference.

According to some examples, the detection circuit 225 may detect the physiologic perturbation using a second implantable sensor circuit 240. The second implantable sensor circuit 240 produces a second electrical sensor signal related to one or more physiologic cardiovascular events in the subject. For example, if the physiologic perturbation is patient exercise, the second implantable sensor circuit 240 includes an activity sensor to provide a signal representative of an activity level of the subject, such as an accelerometer for example. The detection circuit 225 is configured to detect that a physical activity level of the subject exceeds a threshold activity level from the signal.

As described above, when a patient exercises, their heart rate and cardiac stroke volume increases. The increase in heart rate decreases the cardiac cycle length and shifts the S1 and S2 heart sounds in time. The increase in stroke volume due to the exercise changes the amplitudes of the S1 and S2 heart sounds. Therefore, a shift in the S1 and S2 heart sounds and an increase in amplitudes of one or both heart sound are features that correlate to stroke volume and can be used to monitor a physiologic change in stroke volume.

In some examples, the physiologic perturbation is a change in posture of the patient. The second implantable sensor circuit 240 includes a posture sensor and the detection circuit 225 is configured to detect a change in posture of the subject. Changes in contractility of the subject's heart are reflected in heart sounds. A change in posture changes the preload of the heart. A change in contractility may be reflected in a change in timing intervals of the heart sounds and/or in the amplitude of the S1 heart sound. For example, in a weak left ventricle the isovolumic contraction time is prolonged; resulting in a wide S1 complex or long S1 duration. Also, the occurrence of the S1 complex may be delayed. Therefore, S1 width, S1 amplitude, and a time shift in S1 are features that correlate to contractility and can be used to monitor a physiologic change in contractility.

In some examples, the physiologic perturbation is a change in phase of a circadian cycle or pattern of the subject, (e.g., waking or sleeping). The processor circuit 215 may include a timer circuit 245. The processor circuit 215 triggers the heart sound feature circuit to identify a heart sound feature in relation to a phase of a circadian pattern of the subject.

In some examples, the physiologic perturbation is a drug therapy received by the subject. If the heart sounds change (e.g., amplitude) in response to a drug therapy (e.g., a diuretic intake), this may indicate that the renal function is not resistant to the drug therapy. Therefore, a change in amplitude of heart sounds may be a feature that correlates to a drug therapy's impact on renal function. In certain examples, the processor circuit uses the timer circuit 245 to trigger the heart sound feature circuit in relation to a time the subject receives the drug therapy. In some examples, the IMD 205 includes a drug reservoir and administers a drug therapy to the subject such as by a positive displacement pump mechanism for example. The processor circuit 215 triggers the heart sound feature circuit in a time relation to a delivery of drug therapy to the subject.

Figure 3:
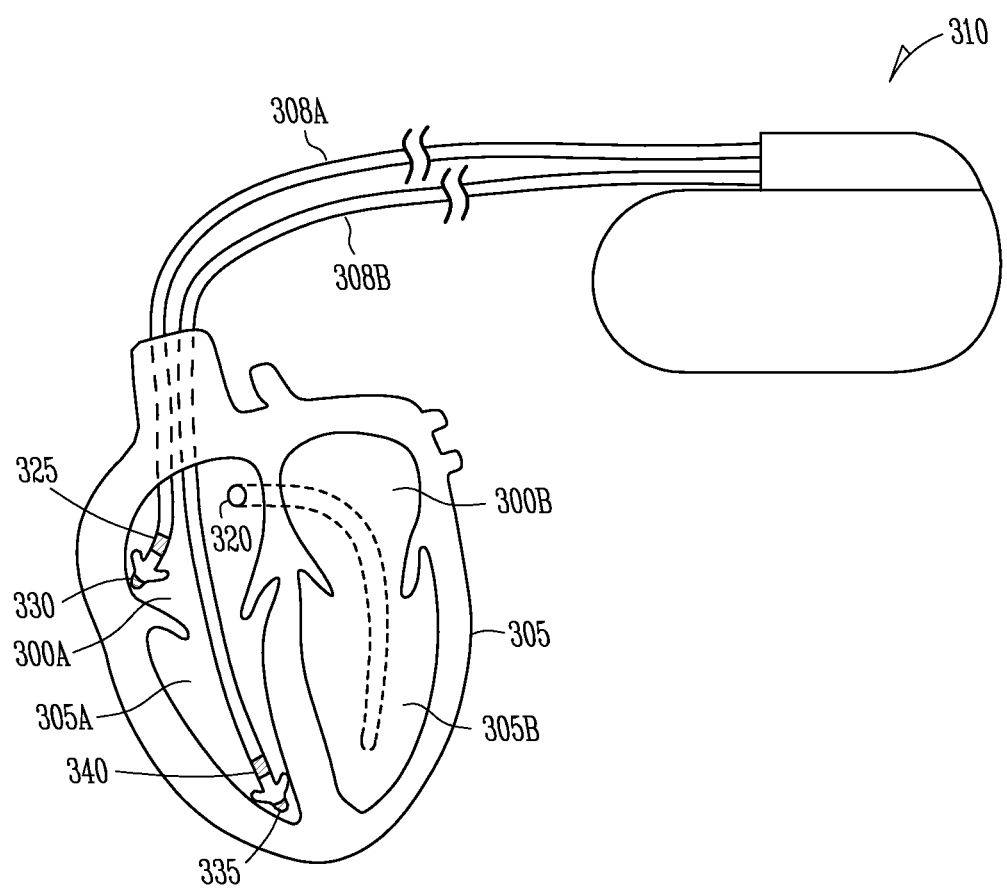
FIG. 3 illustrates an example of an IMD coupled to a heart by one or more leads.

FIG. 3 illustrates an example of an IMD 310 coupled to heart 305, such as by one or more leads 308A-B. Heart 305 includes a right atrium 300A, a left atrium 300B, a right ventricle 305A, a left ventricle 305B, and a coronary vein 320 extending from right atrium 300A. In this embodiment, atrial lead 308A includes electrodes (electrical contacts, such as ring electrode 325 and tip electrode 330) disposed in, around, or near a right atrium 300A of heart 305 for sensing signals, or delivering pacing therapy, or both, to the right atrium 300A. Lead 308A optionally also includes additional electrodes, such as for delivering atrial cardioversion, atrial defibrillation, ventricular cardioversion, ventricular defibrillation, or combinations thereof to heart 305. Lead 308A optionally further includes additional electrodes for delivering pacing or resynchronization therapy to the heart 305.

Ventricular lead 308B includes one or more electrodes, such as tip electrode 335 and ring electrode 340, for sensing signals, for delivering pacing therapy, or for both sensing signals and delivering pacing therapy. Lead 308B optionally also includes additional electrodes, such as for delivering atrial cardioversion, atrial defibrillation, ventricular cardioversion, ventricular defibrillation, or combinations thereof to heart 305. Such electrodes typically have larger surface areas than pacing electrodes in order to handle the larger energies involved in defibrillation. Lead 308B optionally further includes additional electrodes for delivering pacing or resynchronization therapy to the heart 305.

Other forms of electrodes include meshes and patches which may be applied to portions of heart 305 or which may be implanted in other areas of the body to help "steer" electrical currents produced by IMD 310. In one embodiment, one of atrial lead 308A or ventricular lead 308B is omitted, i.e., a "single chamber" device is provided, rather than the dual chamber device illustrated in FIG. 3. In another embodiment, additional leads are provided for coupling the IMD 310 to other heart chambers and/or other locations in the same heart chamber as one or more of leads 308A-B. The present methods and systems will work in a variety of configurations and with a variety of electrical contacts or "electrodes," including a leadless system that uses electrodes remote from, rather than touching, the heart 305.

Returning to FIG. 2, in some examples, the second implantable sensor circuit 240 includes a cardiac signal sensing circuit. The cardiac signal sensing circuit includes one or more sense amplifiers in electrical communication with electrodes to provide an electrical representative of an intrinsic cardiac signal of the subject.

Baroreflex sensitivity (BRS) is a measure of the gain in the resulting recovery in blood pressure and is typically measured using units of milliseconds per millimeters of mercury (ms/mmHg). BRS has been shown to be a good prognostic indicator. For example, Mean arterial pressure (MAP) recovery is used to assess a patient's hemodynamic tolerance to a tachyarrhythmia. BRS correlates well to MAP recovery during ventricular tachyarrhythmia and for this reason BRS is a good measure of hemodynamic stability during tachyarrhythmia. An indication of a subject's BRS can be established by measuring blood pressure and monitoring heart rate.

In certain examples, the physiologic perturbation includes a sensed premature ventricular contraction (PVC) and the detection circuit 225 is configured to detect a PVC. A PVC refers to two ventricular contractions occur (V-V interval), without an intervening atrial contraction. An indication of BRS indicator is a measure of the gain in the resulting recovery in blood pressure after the PVC. The gain can be viewed as the slope of a graph of V-V intervals versus change in blood pressure. A higher slope reflects higher BRS and a lower slope reflects lower BRS. Descriptions of systems and methods that monitor the baroreflex sensitivity of a subject are found in Ettori et al., U.S. patent application Ser. No. 11/457,644, "Baroreflex Sensitivity Monitoring and Trending for Tachyarrhythmia Detection," filed Jul. 14, 2006, published as U.S. Patent Application Publication No. 20080015651 which is incorporated herein by reference.

A change in blood pressure may be reflected in a change in heart sounds such as the amplitude of the heart sounds and/or the power spectrum of the heart sounds for example. Therefore, heart sound amplitude and heart sound power spectrum are features that correlate to blood pressure and can be used as a surrogate to monitor a physiologic change in BRS.

In certain examples, the physiologic perturbation includes a heart rate that exceeds a threshold heart rate, and the detection circuit 225 is configured to detect when a heart rate of the subject exceeds a threshold heart rate value. A change in one or more heart sound intervals are features that are useful to monitor heart rate variability.

According to some examples, the physiologic perturbation includes modulation of the subject's hemodynamics due to respiration. In certain examples, the second implantable sensor circuit 240 includes a respiration sensor to provide a signal representative of respiration of the subject, and the detection circuit 225 is configured to detect a phase of a respiration cycle of the subject from the signal. An example of an implantable respiration sensor is a transthoracic impedance sensor to measure minute respiration volume. An approach to measuring transthoracic impedance is described in Hartley et al., U.S. Pat. No. 6,076,015, "Rate Adaptive Cardiac Rhythm Management Device Using Transthoracic Impedance," filed Feb. 27, 1998, which is incorporated herein by reference.

Modulation of hemodynamics due to respiration is another example of a physiologic perturbation that changes heart sounds. During end-inspiration, the cardiac stroke volume may increase which in turn increases heart sound amplitude. Also, an increase in cardiac stroke volume shifts the timing of the opening and closing of the cardiac valves and hence shifts the timing of the heart sounds.

Figure 4:
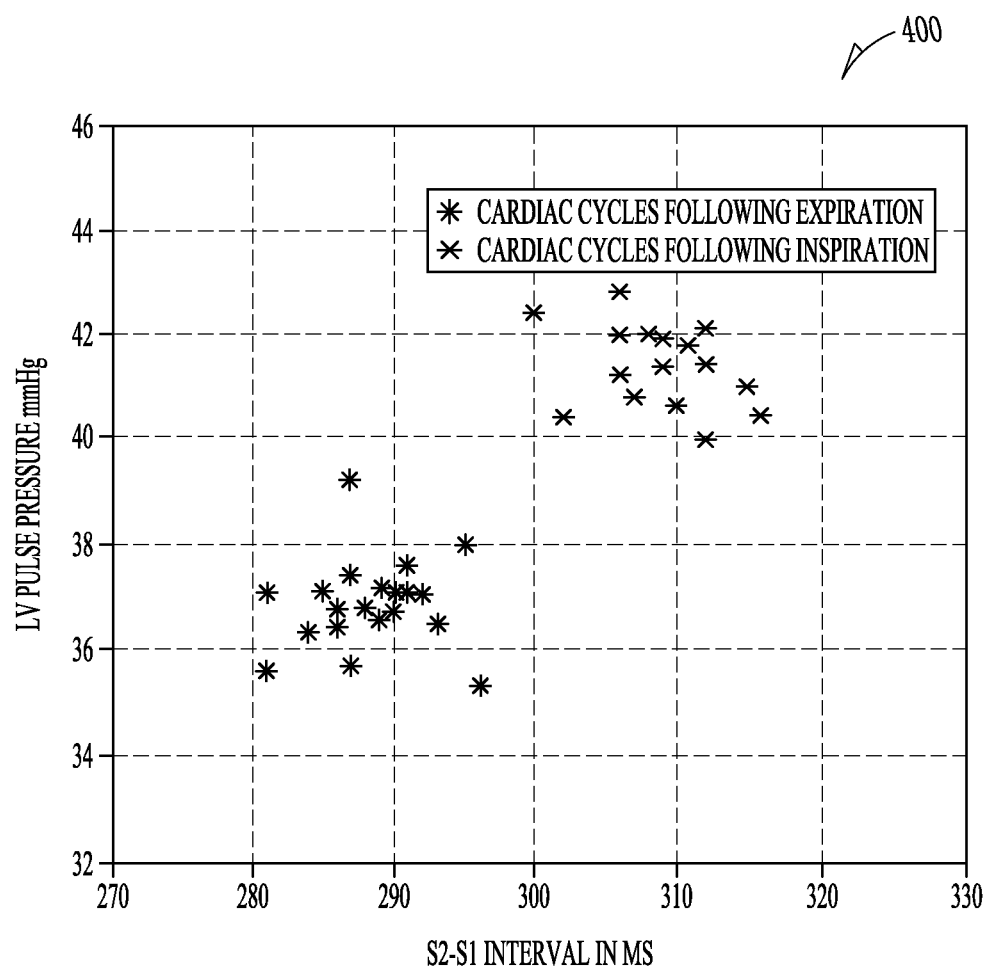
FIG. 4 shows a graph illustrating S2-S1 time intervals for inspiration and expiration.

FIG. 4 shows a graph 400 illustrating S2-S1 time intervals for inspiration and expiration. The graph 400 shows that the S2-S1 time interval is longer after inspiration than expiration. This difference is time intervals is due to a change in stroke volume and is also reflected in a difference in left ventricle (LV) pressure. The graph shows that LV pressure is higher for inspiration, and thus the amplitude of the S2 and S1 heart sounds will be greater for inspiration. Therefore, the S2-S1 interval and the heart sound amplitude are features that correlate to stroke volume and can be used to monitor a physiologic change in stroke volume. Descriptions of systems and methods for monitoring heart sounds in relation to respiration are found in the above mentioned Haro et al., "Respiration-Synchronized Heart Sound Trending," which is incorporated herein by reference.

As described above, heart sound features may correlate to a drug therapy's impact on renal function. A drug therapy's impact on renal function may also be reflected in a change in thoracic impedance. Thus, measuring transthoracic impedance in conjunction with monitoring heart sounds is useful to monitor a drug therapy's impact on renal function.

When a perturbation is detected using the detection circuit 225 of FIG. 2, the processor circuit 215 triggers the heart sound feature circuit 230 in relation to the perturbation to identify a heart sound feature in the electrical signal representative of the heart sound. Examples of heart sound features include, without limitation, an interval between heart sounds (e.g., an interval between the S1 and the S2 heart sounds in FIG. 1), a duration of a heart sound (e.g., the duration or width of the S1 heart sound), an amplitude of a peak of a heart sound (e.g., a zero-to-peak amplitude or a peak-to-peak amplitude of a heart sound) or a power spectrum of a heart sound. Descriptions of systems and methods for additional heart sound measurements are found in Patangay et al., U.S. patent application Ser. No. 11/625,003, "Ischemia Detection Using Heart Sound Timing," filed Jan. 19, 2007, published as U.S. Patent Application Publication No. 20080177191, now issued as U.S. Pat. No. 7,736,319, which is incorporated by reference.

The trending circuit 235 trends the identified heart sound features in relation to a recurrence of the physiologic perturbation. The goal is to choose a heart sound feature providing the desired information about the patient, identify the feature in relation to the physiologic perturbation using the heart sound feature circuit 230, and trend the feature over time to determine whether there is a change in a physiologic condition of the patient according to the trending. The trending determines a measurable margin of change in an aspect of the pathological condition to uncover a subclinical pathologic change. Examples of the trending include, without limitation, trending to determine a change in decompensation (heart failure), a change in sympathetic activity, a change in patient response to a drug therapy, and a change in cardiac contractility.

In some examples, the IMD 205 includes a communication circuit to communicate information wirelessly to an external device, such as by mutual induction, radio frequency (RF), or another telemetry method. The IMD 205 communicates an indication of the change in the physiologic condition to an external device. The indication is then available to a user, such as a clinician or caregiver, or is available to a third device in communication with the external device.

In some examples, the IMD does not necessarily include the trending circuit 235, and the trending is done by the external device, such as an IMD programmer or a server that is part of a patient management system. The IMD 205 includes a communication circuit to communicate information about one or more heart sound features to the external device. The external device trends a feature over time to determine whether there is a change in a physiologic condition of the patient according to the trending.

The physiologic perturbation used to trigger the feature identification of the heart sound signal may be sensed and occur naturally, or the perturbation may be induced. The perturbation may be induced by causing some action by the subject (e.g., forced breathing by the patient to cause a PVC) or the perturbation may be induced by the IMD 205. In some examples, the IMD 205 includes a therapy circuit 250. The therapy circuit 250 provides a therapy (e.g., pacing therapy) to the subject. The processor circuit 215 initiates a therapy to induce the physiologic perturbation and to trigger the heart sound feature circuit 230 in a time relation to the therapy.

A pacing pulse provided by the therapy circuit 250 can be viewed as an induced PVC. For example, the processor circuit 215 may initiate two ventricular contractions or a ventricular contraction after an intrinsic ventricular contraction before an intervening atrial contraction occurs. The processor circuit 215 initiates the PVC and triggers the heart sound feature circuit 230 in a time relation to the PVC. Thus, heart sound features can be monitored in relation to a PVC without having to wait for a sensed occurrence of a PVC.

Because pacing therapy may cause a change in synchrony of a cardiac contraction, pacing therapy is also a physiologic perturbation. If the chambers (e.g., the ventricles) of the heart are dyssynchronous, pacing synchronizes the contraction by activating delayed myocardial regions with those regions that activate earlier. Subjects with heart failure (HF) may have a dyssynchrony of heart chambers. Pacing the chambers to restore coordination of the contractions increases the stroke volume of the heart and therefore changes the heart sounds.

Figure 5:
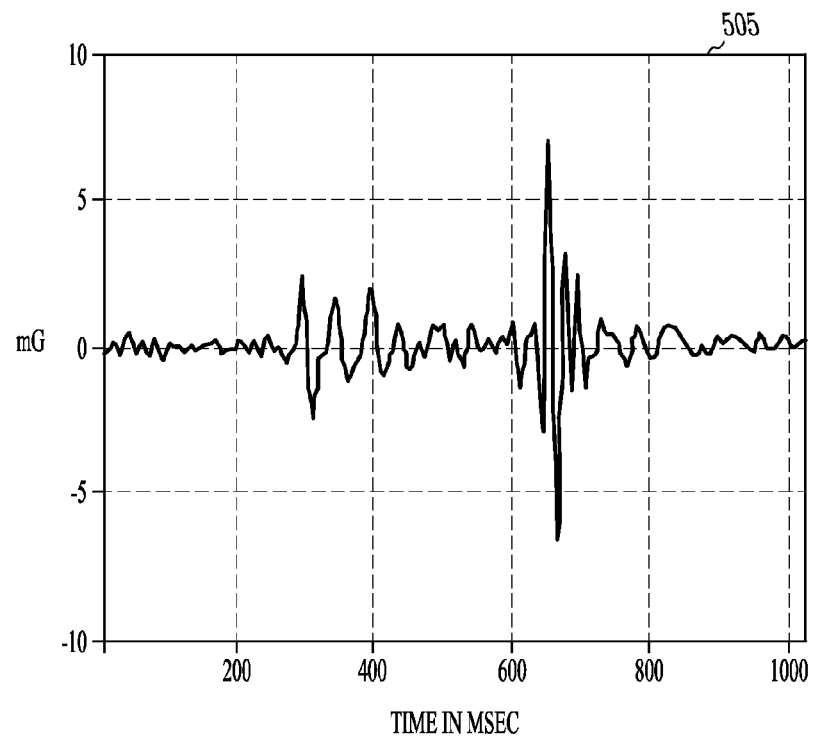
FIG. 5 shows a graph illustrating S1 and S2 heart sounds without pacing the left ventricle (LV), and a graph illustrating heart sounds with pacing the LV.
Figure 5:
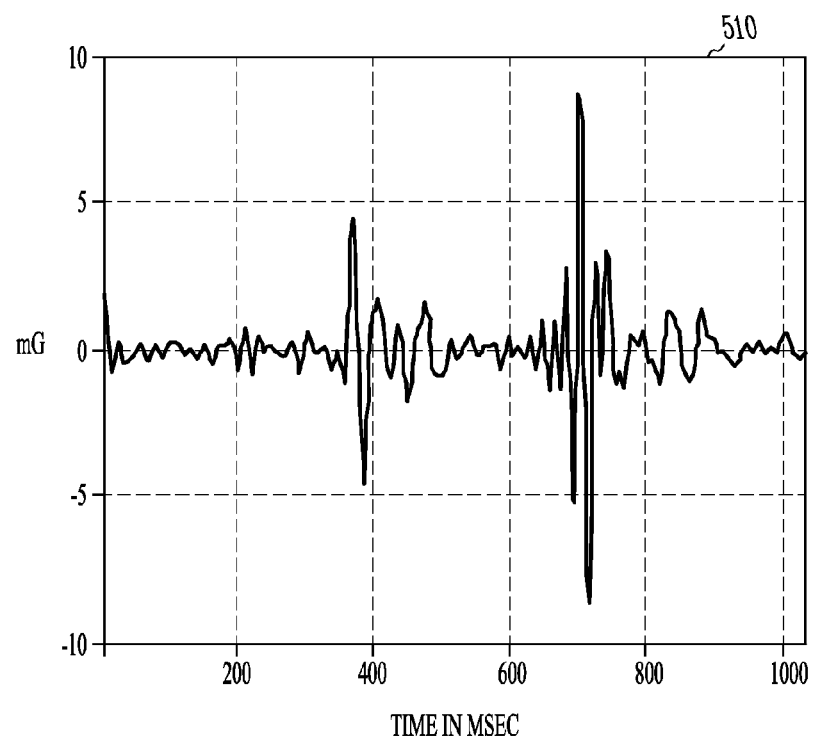

FIG. 5 shows a graph 505 illustrating S1 and S2 heart sounds without pacing the left ventricle (LV) to synchronize contractions with the right ventricle (RV), and a graph 510 illustrating heart sounds with pacing to synchronize the LV with the RV. It can be seen in the graphs that pacing the left ventricle synchronous with the right ventricle increases the amplitude of the 51 and S2 heart sound. In the IMD of FIG. 2, the processor circuit 215 initiates a paced cardiac contraction as the physical perturbation and triggers the heart sound feature circuit 230 in a time relation to the paced cardiac contraction.

Figure 6:
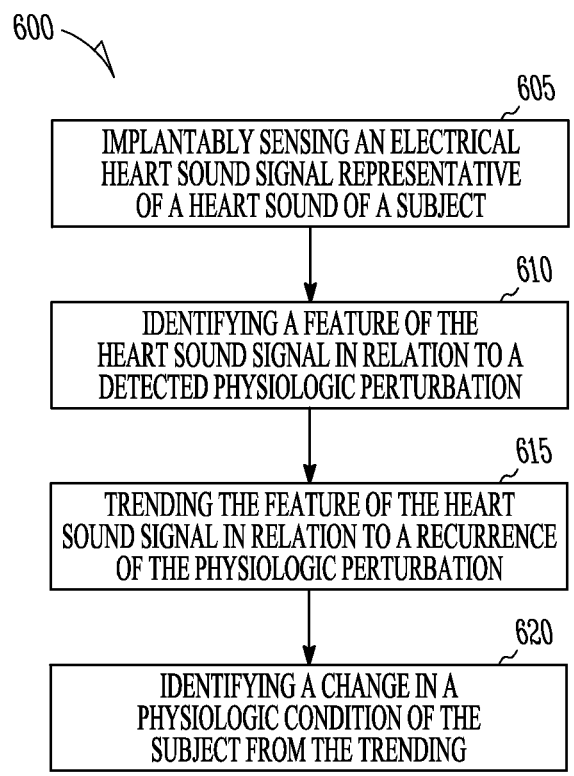
FIG. 6 shows a flow diagram of an example of a method for monitoring heart sounds.

FIG. 6 shows a flow diagram of an example of a method 600 for monitoring heart sounds. At 605, an electrical heart sound signal representative of a heart sound of a subject is implantably sensed. At 610, a feature of the heart sound signal is identified in relation to a detected physiologic perturbation. At 615, the feature is trended in relation to a recurrence of the physiologic perturbation. At 620, a change in a physiologic condition of the subject is identified from the trending.

Many heart sound features have been described as being of interest to different physiologic pathologies. A non-exhaustive list of these features have included durations of heart sounds, intervals between heart sounds, amplitudes of heart sounds and power spectrums of heart sounds. Thus, heart sounds have multiple components or features and the features may be represented in the time domain or the frequency domain.

Figure 7:
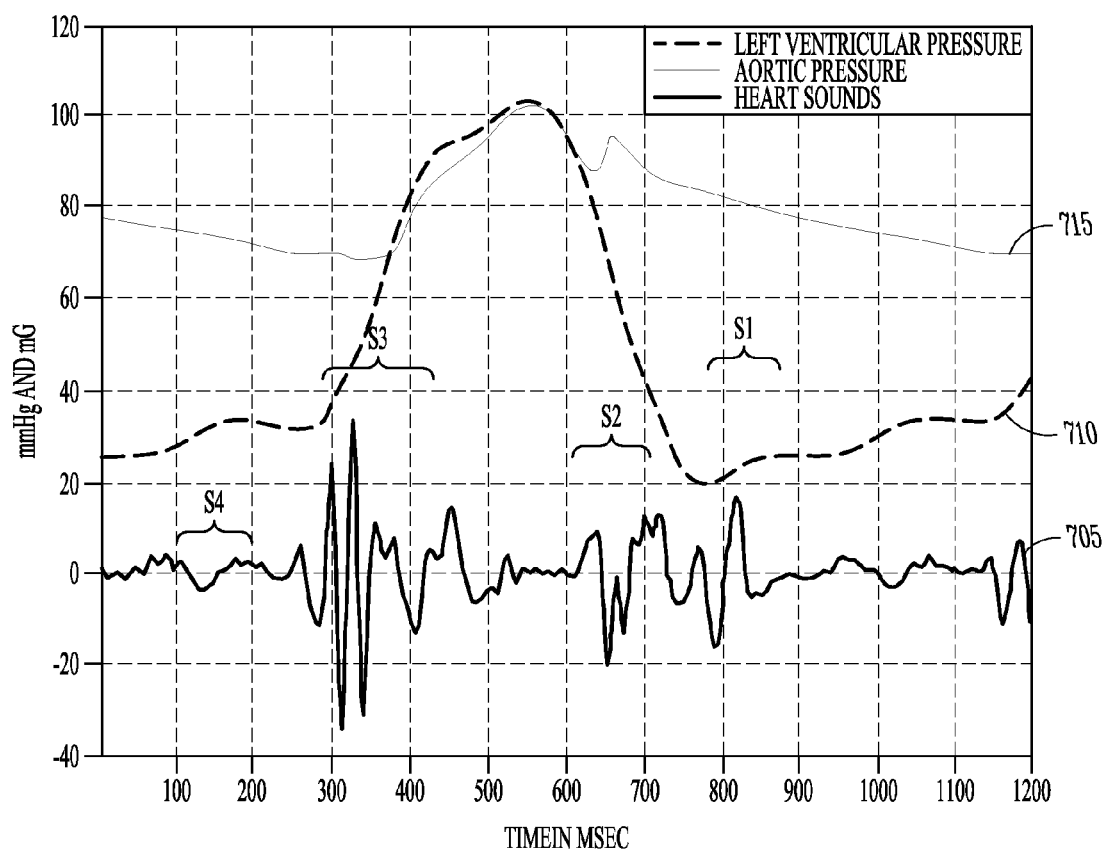
FIG. 7 shows a heart sound graph of S1-S4 heart sounds recorded synchronously with a LV pressure graph and an aortic pressure graph.

FIG. 7 shows a heart sound graph 705 of the S1-S4 heart sounds recorded synchronously with a LV pressure graph 710 and an aortic pressure graph 715. It can be seen in the graphs that the different components of the S1 waveform have different frequency localization properties. For example, the early portion of S1, associated with the mitral valve has a higher frequency than the later portion of the S1 heart sound associated with blood ejecting after opening of the aortic valve. The mitral component is typically localized around 30-60 hertz (Hz) whereas the aortic component is typically localized around 15-25 Hz.

While there is much information regarding the localization and amplitudes of various heart sounds components contained in the time-frequency domain of heart sounds, this information is not consistent across different patho-physiologic states. For example, in patients with reduced contractility with mitral regurgitation, the mitral component of the S1 heart sound is diminished due to leaky valves. Each patient or subject may have a unique pathology that giving the heart sounds of the patient a unique time-frequency footprint with patho-physiologic information related to the patient's disease state. This time-frequency footprint contains information that, when extracted, can be used for clinical applications.

Wavelet filtering can be used to extract information from signals generated by heart sound sensors to detect valvular regurgitation (VR). Wavelet analysis decomposes an electrical signal with both frequency and time. Therefore, the signal energy information includes variations of the amplitude of the electrical signal with both frequency and time.

In wavelet analysis, a scalable modulated window is typically shifted along the time domain electrical signal and for every position the frequency spectrum is calculated. This process is typically repeated many times with a slightly shorter (or longer) window for every new cycle of the electrical signal. By using a variable width window, wavelet analysis effectively zooms in on the signal when analyzing higher frequencies, thus providing higher resolution when necessary. The result is a collection of time-frequency representations of the signal having different resolutions.

The time-frequency representations of the signal can then be decomposed into component signals. Many different wavelet functions can be used to decompose the input electrical signal into component parts. In some examples, Daubechies wavelets are used. The ability of a wavelet function to decompose a signal into its component parts depends on how closely the wavelet used approximates the electrical signal.

Figure 8:
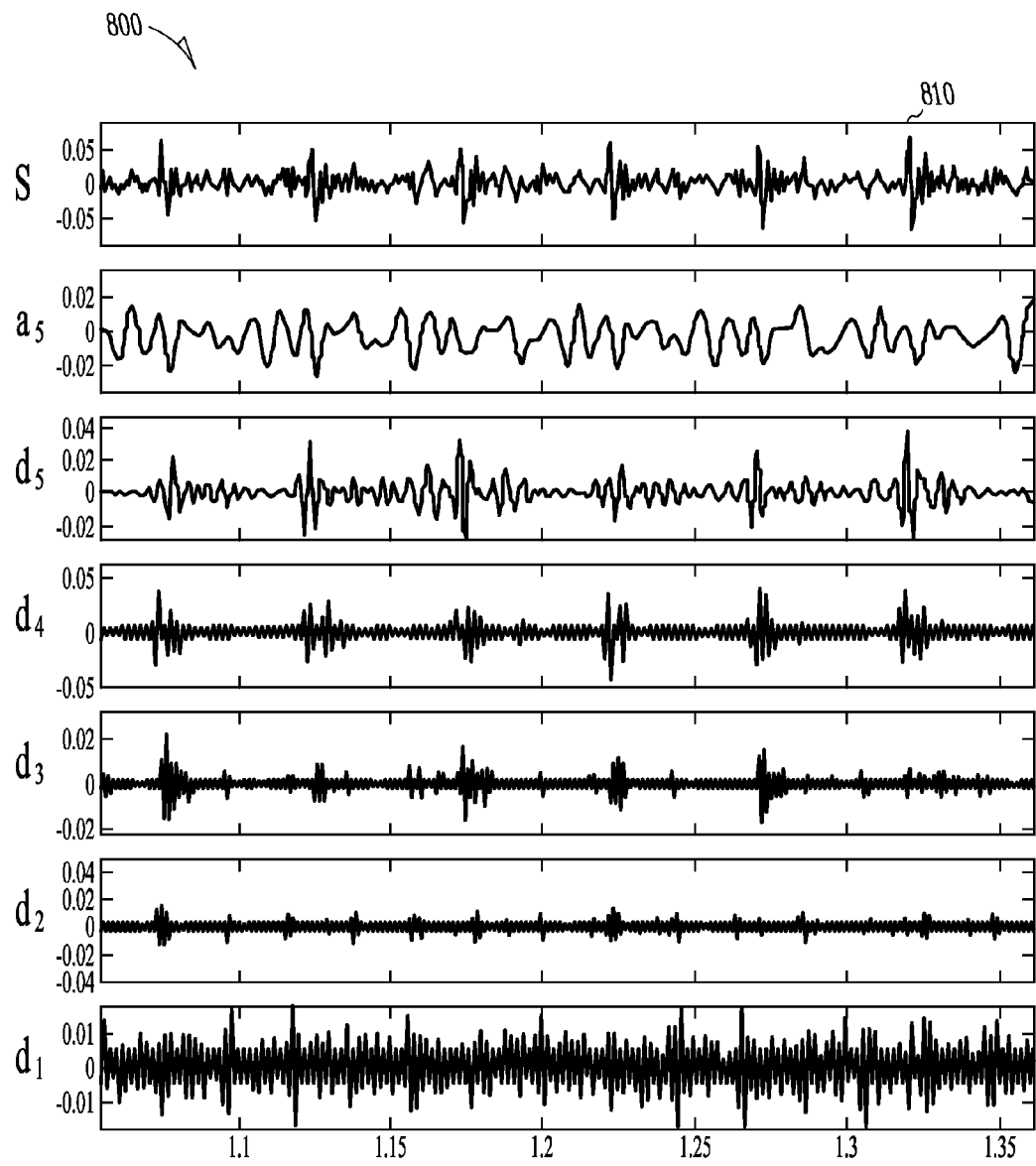
FIG. 8 shows graphical representations of the decomposition of an electrical signal obtained from a heart sound sensor.

FIG. 8 shows graphical representations 800 of the decomposition of the electrical signal obtained from the heart sound sensor. An electrical signal 810 is shown in the top graph. In this example, the decomposition is performed by running the electrical signal 810 through a bank of bandpass filters corresponding to the Daubechies wavelets to obtain the six individual decomposed element signals a5, d5, d4, d3, d2, and d1.

In some examples, the heart sound feature circuit 230 includes a wavelet filter circuit to decompose an electrical heart sound signal into component signals. Descriptions of systems and methods for monitoring heart sounds using wavelet filtering are found in Patangay et al., U.S. Patent Application Publication No. 20070123943, "Systems and Methods for Valvular Regurgitation Detection," filed Nov. 28, 2005, now issued as U.S. Pat. No. 8,108,034, which is incorporated herein by reference.

In some examples, once a feature is identified, the heart sound feature circuit 230 preprocesses subsequent heart sound signals (e.g., from subsequent cardiac cycles) by decomposing the heart sound signals into component signals. In certain examples, the heart sound feature circuit includes a threshold detector to detect one or more heart sound features of interest.

In some examples, the heart sound feature circuit 230 of FIG. 2 identifies heart sound signal features using a comparison to a heart sound template. The IMD 205 includes a memory to store one or more heart sound templates, which include previously attained heart sound information from the subject. The heart sound template includes at least one heart sound feature, such as a morphological feature. The heart sound feature circuit 230 uses a cross-correlation between a heart sound signal and at least a portion of the heart sound template to identify features in the heart sound signal. Descriptions of system and methods to identify heart sound features using a heart sound template are found in Patangay et al., U.S. patent application Ser. No. 11/736,055, "Heart Sound Tracking System and Method," filed Apr. 17, 2007, published as U.S. Patent Application Publication No. 20080262368, now issued as U.S. Pat. No. 7,853,327, which is incorporated by reference.

There may be difficulty in identifying features in heart sound signals for trending over subsequent cardiac cycles because variation in features may cause feature misdetections. A solution is to use information from previous and/or the current heart sound beat to reduce the misdetections. In some examples, the heart sound feature circuit 230 calculates a feature metric. A heart sound feature is tracked by optimizing the feature metric to find the most consistent heart sound feature or set of features. Descriptions of systems and methods to track heart sound features using optimization of a feature metric are found in the above mention Patangay et al., "Heart Sound Tracking System and Method."

Different pathologies of a patient may emphasize different individual components or features of heart sounds. As described above, a pathology may include a change to multiple heart sound features. Although detecting an occurrence of a heart sound, such as S1, may be relatively straightforward, determining which feature of the heart sound is the most sensitive to changes in systolic performance results in analyzing the heart sound complex over time. Because it is desired to find an optimum feature for trending, the physiologic perturbation is used to create a change in the features of the heart sound. When multiple heart sound signal features or components are identified, the identified candidate features can be ranked to determine which feature allows for correct and consistent physiologic variable measurements.

Figure 9:
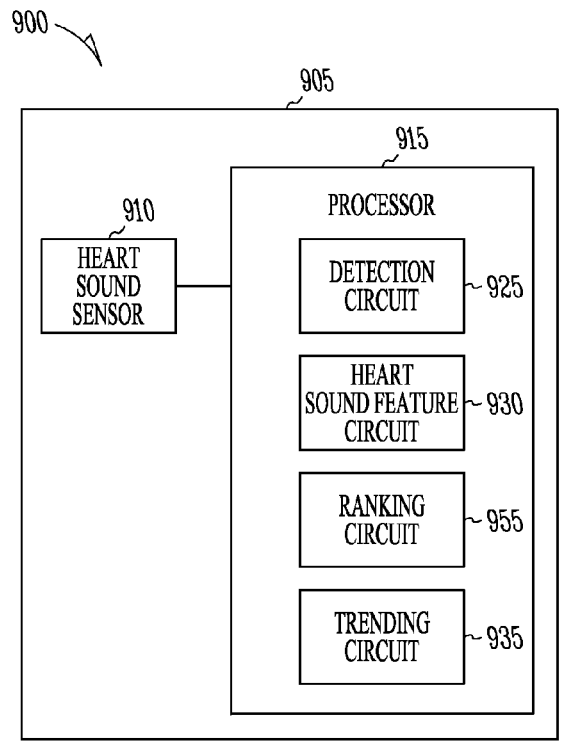
FIG. 9 shows a block diagram of portions of another example of a system for monitoring one or more heart sounds.

FIG. 9 shows a block diagram of portions of another example of a system 900 for monitoring one or more heart sounds. The system 900 includes an IMD 905 that in turn includes an implantable heart sound sensor circuit 910 and processor circuit 915. The processor circuit includes a detection circuit 925 to detect a physiologic perturbation and a heart sound feature circuit 930 to identify one or more heart sound features in the electrical heart sound signal. The processor circuit 915 is configured to trigger the heart sound feature circuit 930 in relation to a detected physiologic perturbation.

The processor circuit 915 also includes a ranking circuit 955 to rank identified candidate heart sound features and select a heart sound feature for trending according to the ranking. The ranking circuit 955 may rank the candidate features by giving a greater weight to candidate features of interest to the physiologic condition of the subject. For example, the ranking circuit 955 may give greater weight to a duration or width of the S1 heart sound when the physiologic condition of the subject relates to contractility and the IMD 905 is searching for a feature to trend contractility, than when the physiologic condition of the subject relates to drug therapy and the IMD 905 is searching for a feature to trend efficacy of the drug therapy.

According to some examples, the ranking circuit 955 uses a linear discriminant analysis classifier to rank the features. In certain examples, the linear discriminant analysis classifier uses Fischer's separability criterion to rank variables to train the classifier. In a regression problem where a set of inputs is used to predict an output variable, a correlation coefficient can be used to estimate the variability in the output due to a given input. A linear or non-linear fit can be used to calculate the correlation coefficient. Weighting can also be added to certain candidate features during the training of the classifier.

In some examples, the ranking circuit 955 uses entropy based (information theoretic) criteria to rank the candidate features. The estimated densities of discrete variables are used to calculate the mutual information between the input variables and the output to rank the candidate features. In some examples, the ranking circuit 955 ranks the candidate features using Chi-Square analysis. In some examples, the ranking circuit 955 ranks the candidate features using an analysis of variance (ANOVA) type statistical tests to rank the candidate features.

Once a heart signal feature or set of features to trend has been identified from the candidate features, the trending circuit 935 trends the heart sound feature in relation to a recurrence of the physiologic perturbation. The processor circuit 915 declares a change in a physiologic condition of the patient according to the trending.

Figure 10:
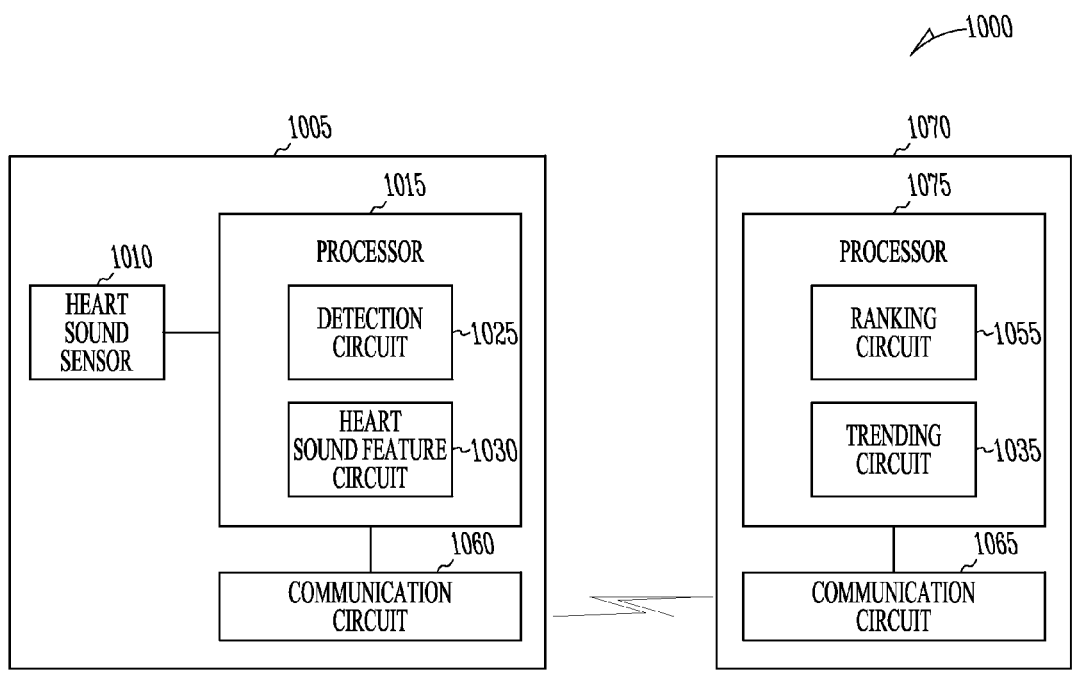
FIG. 10 shows a block diagram of portions of a further example of a system for monitoring one or more heart sounds.

In some examples, the trending and the ranking are done by a second device. FIG. 10 shows a block diagram of portions of another example of a system 1000 for monitoring one or more heart sounds. The system 1000 includes an IMD 1005 and an external device 1070. The IMD 1005 includes an implantable heart sound sensor circuit 1010 and a first processor circuit 1015. The processor circuit 1015 includes a detection circuit 1025 to detect a physiologic perturbation and a heart sound feature circuit 1030 to identify one or more heart sound features in the electrical heart sound signal. The processor circuit 1015 triggers the heart sound feature circuit 1030 in relation to a detected physiologic perturbation. The processor circuit 1015 communicates information about one or more heart sound signal features to the external device using the communication circuit 1060.

The external device 1070 includes a second processor circuit 1075 and communication circuit 1065 to communicate information with the IMD. Examples of the external device include an IMD programmer or a server. The IMD 1005 may communicate to the external device 1070 using a third device, such as a repeater for example. The processor circuit 1075 includes a trending circuit 1035 to trend the heart sound feature in relation to a recurrence of the physiologic perturbation. The processor circuit 1075 declares a change in a physiologic condition of the patient according to the trending. The processor circuit 1075 may provide an indication of the change to a user or a caregiver, such as by a display on the external device 1070 for example. The processor circuit 1075 may provide the indication to another process, such as a third device in communication with the external device via a communication network such as a computer network (e.g., the internet) or a cell phone network.

In some examples, the heart sound feature circuit 1030 of the IMD 1005 identifies a plurality of candidate heart sound features and the processor circuit 1015 communicates information about the heart sound signal features to the external device using the communication circuit 1060. The processor 1075 includes a ranking circuit 1055 to rank the candidate heart sound features and select a heart sound feature for trending according to the ranking.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
    an implantable heart sound sensor circuit configured to produce an electrical heart sound signal representative of a heart sound of a subject;
    a physiological sensor configured to produce a physiological signal representative of activity of the subject;
    a processor circuit coupled to the heart sound sensor circuit and the second sensor circuit, wherein the processor circuit includes:
        a detection circuit configured to detect a change in phase of a circadian cycle of the subject using the physiological signal;
        a heart sound feature circuit configured to identify a heart sound feature in the electrical heart sound signal in relation to a specified phase of the circadian cycle; and
        a trending circuit configured to trend the identified heart sound feature during the specified phase of the circadian cycle, and wherein the processor circuit is configured to generate an indication of a change in a physiologic condition of the subject according to the trend and provide the indication to a user or process.

2. The system of claim 1, wherein the trending circuit is configured to trend a difference between the identified heart sound feature during the specified phase of the circadian cycle and outside the specified phase of the circadian cycle.

3. The system of claim 1, wherein the trending circuit is configured to calculate a difference between the identified heart sound feature during the specified phase of the circadian cycle and outside the specified phase of the circadian cycle, and to trend a change in the difference between the identified heart sound feature during the specified phase of the circadian cycle and outside the specified phase of the circadian cycle.

4. The system of claim 1, wherein the heart sound feature circuit is configured to identify the heart sound feature during a phase of the circadian cycle when the patient is awake and the trending circuit is configured to generate a measurement of the identified heart sound feature when the subject is awake and trend the measurement of the identified heart sound feature.

5. The system of claim 4, wherein the heart sound feature circuit is configured to identify a feature of an S3 heart sound.

6. The system of claim 1, wherein the physiological sensor includes a posture sensor and the physiological signal is representative of posture of the subject.

7. The system of claim 1, wherein the physiological sensor includes an accelerometer and the physiological signal is an acceleration signal.

8. The system of claim 1, wherein the detection circuit is configured to detect a change from a sleeping phase to a waking phase of the circadian cycle, and wherein the heart sound feature circuit is configured to identify the heart sound feature when the patient is awake.

9. The system of claim 1, wherein the processor circuit includes a timer circuit, and wherein the detection circuit is configured to detect a circadian cycle of the subject using the timer circuit.

10. The system of claim 1, wherein the physiological sensor circuit includes a physical activity sensor to provide a signal representative of a physical activity level of the subject, and wherein the detection circuit is configured to detect that a physical activity level of the subject exceeds a threshold activity level from the signal to trigger the heart sound feature circuit.

11. A method of operating a medical device, the method comprising:
sensing a physiological signal representative of activity of a subject;
detecting a change in phase of a circadian cycle of the subject using the physiological signal;
sensing an electrical heart sound signal representative of a heart sound of the subject;
identifying a heart sound feature in the electrical heart sound signal in relation to a specified phase of the circadian cycle;
trending the identified heart sound feature during the specified phase of the circadian cycle; and
generating an indication of a change in a physiologic condition of the subject according to the trend and providing the indication to a user or process.

12. The method of claim 11, wherein trending the identified heart sound feature includes trending a difference between the identified heart sound feature during the specified phase of the circadian cycle and outside the specified phase of the circadian cycle.

13. The method of claim 11, wherein trending the identified heart sound feature includes calculating a difference between the identified heart sound feature during the specified phase of the circadian cycle and outside the specified phase of the circadian cycle, and trending a change in the difference between the identified heart sound feature during the specified phase of the circadian cycle and outside the specified phase of the circadian cycle.

14. The method of claim 11, wherein identifying a heart sound feature includes identifying of feature of an S3 heart sound when the subject is awake, and wherein trending the identified heart sound feature includes trending the feature of the S3 heart sound.

15. The method of claim 11, wherein detecting a change in phase of a circadian cycle of the subject includes detecting when the subject is awake using the physiological signal, and wherein trending the identified heart sound feature includes trending the identified heart sound feature only when the subject is awake.

16. The method of claim 11, wherein sensing a physiological signal includes sensing a physiological signal representative of posture of the subject.

17. The method of claim 11, wherein sensing a physiological signal includes sensing an acceleration signal.

18. The method of claim 11, wherein detecting a change in phase of a circadian cycle of the subject includes detecting a change from a sleeping phase to a waking phase of the circadian cycle, and wherein identifying the heart sound feature includes identifying the heart sound feature when the patient is awake.

19. The method of claim 11, wherein detecting a change in phase of a circadian cycle of the subject includes detecting a change in phase according to a timer circuit.

20. The method of claim 11, wherein sensing a physiological signal includes sensing a signal representative of a physical activity level of the subject, and wherein identifying the heart sound feature includes identifying the heart sound feature when a physical activity level of the subject exceeds a threshold activity level.

* * * * *